United States Patent
Joshi et al.

(10) Patent No.: US 9,277,874 B2
(45) Date of Patent: Mar. 8, 2016

(54) FAULT-TOLERANT MULTIELECTRODE ARRAY FOR BRAIN IMPLANTABLE DEVICE

(75) Inventors: Bharat S. Joshi, Pineville, NC (US); Ipsita Acharya, Charlotte, NC (US); Hitten P. Zaveri, New Haven, CT (US)

(73) Assignees: YALE UNIVERSITY, New Haven, CT (US); THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 102 days.

(21) Appl. No.: 14/114,390

(22) PCT Filed: Apr. 27, 2012

(86) PCT No.: PCT/US2012/035439
§ 371 (c)(1),
(2), (4) Date: Oct. 28, 2013

(87) PCT Pub. No.: WO2012/149306
PCT Pub. Date: Nov. 1, 2012

(65) Prior Publication Data
US 2014/0058239 A1 Feb. 27, 2014

Related U.S. Application Data

(60) Provisional application No. 61/479,982, filed on Apr. 28, 2011.

(51) Int. Cl.
*A61B 5/0478* (2006.01)
*A61B 5/0476* (2006.01)

(52) U.S. Cl.
CPC ............ *A61B 5/0478* (2013.01); *A61B 5/0476* (2013.01); *A61B 2560/066* (2013.01); *A61B 2562/04* (2013.01)

(58) Field of Classification Search
CPC .................... A61B 5/04001; A61B 5/0478
See application file for complete search history.

(56) References Cited

U.S. PATENT DOCUMENTS

| | | | | |
|---|---|---|---|---|
| 4,957,109 A | * | 9/1990 | Groeger et al. | 600/391 |
| 5,184,620 A | * | 2/1993 | Cudahy et al. | 600/382 |
| 7,221,981 B2 | * | 5/2007 | Gliner | 607/116 |
| 7,305,268 B2 | * | 12/2007 | Gliner et al. | 607/45 |
| 7,774,052 B2 | * | 8/2010 | Burton et al. | 600/544 |
| 7,917,206 B2 | | 3/2011 | Frei et al. | |
| 8,165,684 B2 | | 4/2012 | Putz et al. | |
| 8,170,656 B2 | * | 5/2012 | Tan et al. | 600/546 |
| 2003/0069514 A1 | * | 4/2003 | Brody | 600/546 |
| 2004/0133119 A1 | | 7/2004 | Osorio et al. | |

(Continued)

OTHER PUBLICATIONS

Acharya, I, et al.: Reconfigurable Fault-Tolerant Multielectrode Array for Dependable Monitoring of the Human Brain. 33rd Int'l. Conf. of the IEEE EMBS, 2011, p. 652-655.

(Continued)

*Primary Examiner* — Lee S Cohen
(74) *Attorney, Agent, or Firm* — Welsh Flaxman & Gitler LLC

(57) ABSTRACT

A multielectrode array with fault-tolerance for use in conjunction with a brain implantable device includes a sensor grid composed of a plurality of sensors, the plurality of sensors including primary sensors and spare sensors. The multielectrode array also includes signal processing circuitry associated with the plurality of sensors and a control system associated with the sensor grid for replacing faulty primary sensors with spare sensors.

4 Claims, 24 Drawing Sheets

A block diagram of the present brain-implantable device including an intracranial electrode/sensor unit, subcutaneous central processing node and an external system.

(56) References Cited

U.S. PATENT DOCUMENTS

| | | | |
|---|---|---|---|
| 2007/0265668 A1 | 11/2007 | Reinke et al. | |
| 2009/0149913 A1 | 6/2009 | Putz et al. | |
| 2011/0093052 A1 | 4/2011 | Anderson et al. | |
| 2011/0125046 A1* | 5/2011 | Burton et al. | 600/544 |
| 2012/0209346 A1 | 8/2012 | Bikson et al. | |
| 2012/0238855 A1 | 9/2012 | Lanning et al. | |

OTHER PUBLICATIONS

Adve, Vikram S., et al., "Parallel Program Performance Prediction Using Deterministic Task Graph Analysis", ACM Transactions on Computer Systems, Feb. 2004, 22(1): 94-136.

Baker, Monya, "From Promising to Practical: Tools to Study Networks of Neurons", Nature Methods, Nov. 2010, 7(11): 877-884.

Chow, Edward Y., et al., "Analytical Redundancy and the Design of Robust Failure Detection Systems", IEEE Transactions on Automatic Control, Jul. 1984, AC-29(7): 603-614.

Dunia, Ricardo, et al., "A Unified Geometric Approach to Process and Sensor Fault Identification and reconstruction: . . . ", Computers Chem. Engang, 1998, 22(7-8): 927-943.

Dunia, Ricardo, et al., "Subspace Approach to Multidimensional Fault Identification and Reconstruction", Aiche Journal, Aug. 1998, 44(8): 1813-1831.

Engel Jr., Jerome, M.D., "Surgical Treatment for Epilepsy", JAMA, Dec. 3, 2008, 300(21): 2548-2550.

Even, Shimon, "Graph Algorithms 2nd Edition" New York: Cambridge University Press, 2012.

Fisher, Robert, et al., "Electrical Stimulation of the Anterior Nucleus of Thalamus for Treatment of refractory Epilepsy", Epilepsia, 2010, 51(5): 899-908.

Fisher, Robert S., et al., "Reassessment: Vagus Nerve Stimulation for Epilepsy: A Report of the Therapeutics and Technology . . . ", Neurology, 1999, 53(4): 666-9.

Fisher, Robert S., M.D., Ph.D., "Therapeutic Devices for Epilepsy", Annals of Neurolgoy, Feb. 2012, 71(2): 157-168.

"ILAE Commission Report—The Epidemiology of the Epilepsies: Future Directions", Epilepsia, 1997, 38(5): 614-618.

Koren I, Krishna CM: Fault-Tolerant Systems. San Francisco: Morgan Kaufmann, 2007, p. 4-9.

Kwan, Patrick, M.D., et al, "Early Identification of Refractory Epilepsy", The New England Journal of Medicine, Feb. 3, 2000, 342(5): 314-319.

Lanning, Bruce, et al., "Emerging Technologies for Brain-Implantable Devices", Epilepsy: The Intersection of Neurosciences, Biology, Mathematics . . . ,CRC Press, 2011, 429-441.

Lebedev, Mikhail A., et al., "Brain-Machine Interfaces: Past, Present and Future", Trends in Neurosciences, 2006, 29(9): 536-546.

Mattson, T., Sanders, B., and Massingill, B., Patterns for Parallel Programming, Addison Wesley Software Patterns Series, 2004, p. 112-121 and 124-126.

Morrell M, RNS System Pivotal Investigators: Results of a multicenter double blind randomized controlled pivotal investigation of the RNS . . . ,Annual Meeting of the AES, 2009.

Papadimitriou CH, Stieglitz K: Combinatorial Optimization, Algorithms and Complexity. Englewood Cliffs, NJ: Prentice-Hall, 1982, p. 117 and 218-227.

Rubehn, Birthe, et al., "A MEMS-Based Flexible Multichannel ECoG-Electrode Array", Journal of Neural Engineering, 2009, 6(3): 1-10.

Su et al. Yield Enhancement of Digital Microfluidics-Based Biochips Using Space Redundancy and Local Reconfiguration. IEEE Computer Society 2005.

\* cited by examiner

A block diagram of the present brain-implantable device including an intracranial electrode/sensor unit, subcutaneous central processing node and an external system.

A schematic of the present brain implantable device with two multielectrode arrays and a central node. An external unit and the data, power, and communication paths are also shown.

An $n \times m$ array of primary modules with $s$ columns of spare modules placed to the right of the array of primary modules.

Reliability as a function of redundancy ratio for a fault-tolerant MEA solution which includes spare columns. Here the number of rows, $n = 100$, fault coverage $C = 1$, $k = n$, and module reliability is assumed to be 0.9.

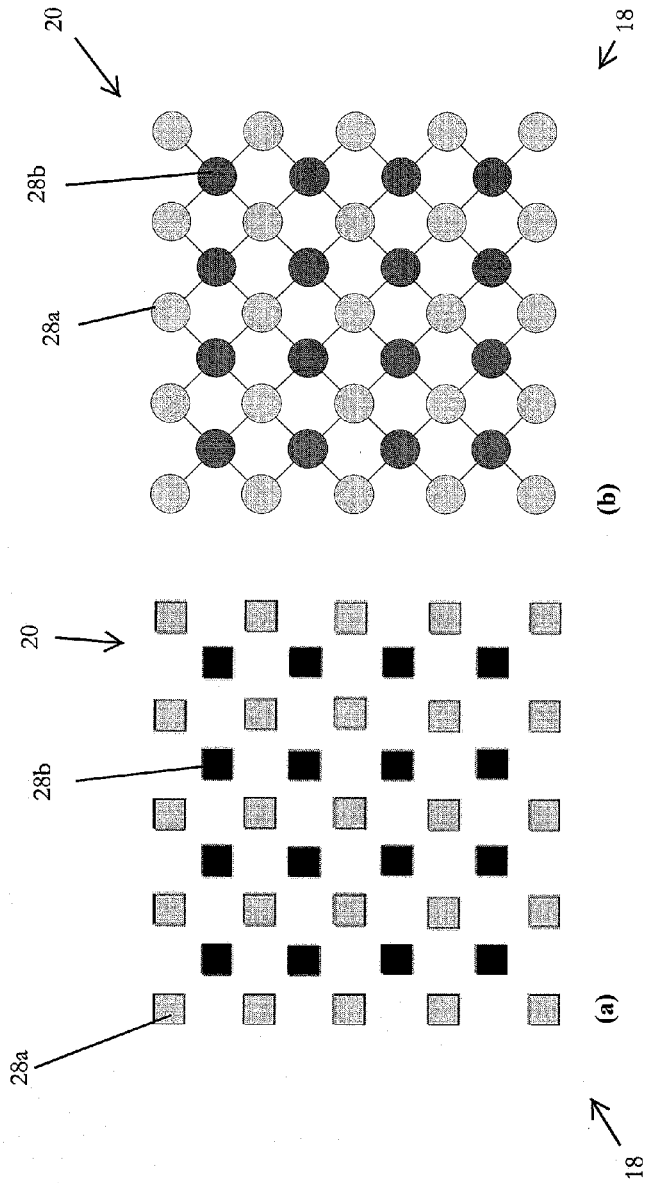

FIGS. 5(a) & 5(b)

(a) An example of (4, 4) IRA with spare modules (black) at the interstitial sites of the primary modules (gray). (b) The corresponding graph model for the (4, 4) IRA shown in (a) where each node in the graph represents a primary or spare module. Note, in the graph representation each primary module is connected to the spare modules which can replace it, and each spare module is connected to the primary modules it can replace.

(a) A (4, 4) IRA with an example set of faults. Here, primary modules (1, 1), (2, 1), (2, 2) and (1, 5) are faulty. (b) The corresponding graph model for the (4, 4) IRA shown in (a). A faulty module is marked with an 'X'.

(a) A subgraph of the four faulty modules shown in Figure 6(a), and all the spare modules which can replace them. This sub-graph is a bipartite graph. (b) A maximum matching solution of the bipartite graph shown in (a). This matching is one possible mapping of faulty primary modules to spare modules to correct the faults in the MEA shown in Figure 6(a).

Directed graph of the network of the bipartite graph in Figure 7(a).

(a) An example of (1, 4) IRA with spare module (black) at the interstitial sites of the primary modules (gray), and (b) the corresponding graph model.

The reliability of (1, 4) IRA MEA with redundancy ratio of 0.25, $C = 1$, and $N = mn = 64, 256, 576$ and $1024$. The (1, 4) IRA MEAs are compared to the corresponding MEAs without redundancy. It is evident that there is an increase in MEA reliability with the IRA solution.

(a) (1, 6) IRA grid design, (b) the corresponding graph model. The gray nodes represent primary modules and the black nodes denote spare modules.

The reliability of (1, 6) IRA MEA with redundancy ratio of 0.25, $C = 1$, and $N = mn = 90$, 540 and 900 compared to the corresponding MEAs without redundancy.

The reliability of (4, 4) IRA MEA with redundancy ratio of 1, $C = 1$, and $N = mn = 64, 256, 576$ and $1024$ compared to the corresponding MEAs without redundancy.

The reliability of a (4, 4) IRA MEA with redundancy ratio of 1, and fault coverage factor, $C = 0.95$, and $N = mn = 64, 256, 576$ and $1024$, and the reliability of the corresponding MEAs without redundancy.

The reliability of a (4, 4) IRA MEA with redundancy ratio=1, and fault coverage factor, $C = 0.90$, and $N = mn = 64, 256, 576$ and $1024$, and the reliability of the corresponding MEAs without redundancy.

(a) (2, 6) IRA grid design, (b) the corresponding graph model. The gray nodes represent primary modules and the black nodes represent spare modules.

The reliability of (2, 6) IRA MEA with redundancy ratio of 0.33, $C = 1$, and $N = mn = 90, 540$ and $900$, and the reliability of the corresponding MEAs without redundancy.

Reliability of (1, 6), (1, 4), (2, 6), and (4,4) IRAs with C = 1 for different sizes and module reliability.

Reliability of a (1, 4) IRA with C =1, 0.9 and 0.95 for MEAs of different sizes and varying module reliability.

Reliability of a (1, 6) IRA with C =1, 0.9 and 0.95 for MEAs of different sizes and varying module reliability.

Reliability of a (2, 6) IRA with C=1, 0.9 and 0.95 for MEAs of different sizes and varying module reliability.

Reliability of a (4, 4) IRA with $C = 1$, 0.9 and 0.95 for MEAs of different sizes and varying module reliability.

Simulation of fault reconfiguration for a (4, 4) IRA with grid size $N = 64$ and with a fault-coverage factor, $C = 1$. There is a steady decrease in percentage system reconfiguration with increasing percentage of primary faults.

Simulation of fault reconfiguration for a (4, 4) IRA with grid size $N = 100$ and with a fault-coverage factor, $C = 1$.

FAULT-TOLERANT MULTIELECTRODE ARRAY FOR BRAIN IMPLANTABLE DEVICE

CROSS-REFERENCE TO RELATED APPLICATIONS

This application is the national phase of International Application No. PCT/US2012/035439, entitled "FAULT-TOLERANT MULTIELECTRODE ARRAY FOR BRAIN IMPLANTABLE DEVICE", filed Apr. 27, 2012, which claims the benefit of U.S. Provisional Patent Application Ser. No. 61/479,982, entitled "FLEXIBLE AND SMART BIO-SIGNAL MONITORING FAULT TOLERANT MULTI-ELECTRODE ARRAY FOR BRAIN IMPLANTABLE DEVICE", filed Apr. 28, 2011.

BACKGROUND OF THE INVENTION

1. Field of the Invention

The invention relates to a fault-tolerant approach to monitoring and intervening with an implantable device in the neurological biosignaling of human patients suffering from disorders such as epilepsy and locked in syndrome. More particularly, the invention relates to a hardware redundancy based fault-tolerant multielectrode array for use with a brain implantable device for monitoring and intervening in the treatment of epilepsy or locked-in syndrome.

2. Description of the Related Art

Epilepsy is one of the most common neurological disorders, affecting 0.4% to 1% of the world's population. Sander J W A S: *ILAE Commission Report The epidemiology of the epilepsies: Future directions*. Epilepsia, 38(5):614-618, 1997. Pharmacology, the first line of treatment for epilepsy, is helpful for controlling seizures in approximately 64% of patients. Kwan P, Brodie M J: *Early identification of refractory epilepsy*. New England Journal of Medicine, 342(5):314-319, 2000. For the remaining approximately 10-20 million patients worldwide with uncontrolled seizures a second line of treatment, where available, is brain surgery [Engel J: *Surgical treatment for epilepsy*. JAMA: The Journal of the American Medical Association, 300(21):2548-2550, 2008.], and a third line of treatment which has emerged in recent years is the use of brain implantable devices [Fisher R S: *Therapeutic Devices for Epilepsy*, Annals of Neurology, 71(2):157-168, 2012]. Currently brain implantable devices employ electrical stimulation to control seizures. Fisher R S, Handforth A: *Reassessment: Vagus nerve stimulation for epilepsy*. Neurology, 53(4):666, 1999; Fisher R, Salanova V, Witt T, et al.: *Electrical stimulation of the anterior nucleus of thalamus for treatment of refractory epilepsy*. Epilepsia, 51(5):899-908, 2010; Morrell M, RNS System Pivotal Investigators: *Results of a multicenter double blind randomized controlled pivotal investigation of the RNS system for treatment of intractable partial epilepsy in adults*. Annual Meeting of the American Epilepsy Society (AES), 2009.

Other implantable devices under development seek to warn of an impending seizure, deliver drugs locally or cool the brain to control seizures. Epilepsy surgery may require multi-day intracranial monitoring of the brain to locate the source of seizures and brain implantable devices to control seizures require permanent monitoring of brain activity to detect or predict a seizure.

Parallel to this effort in epilepsy is an independent effort to develop a brain machine interface (BMI) to detect brain activity and typically activate an external actuator such as a robotic arm or make a decision. Lebedev M A, Nicolelis M A L: *Brain machine interfaces: past, present and future*. Trends in neurosciences, 29:536-546, 2006. In the BMI field the effort is primarily focused on detection and analysis of single unit or multi-unit activity and to a lesser extent on the measurement and analysis of the local field potential. Though there are differences between the epilepsy and BMI fields, there are also similarities in that both fields endeavor to measure neuronal activity directly from the brain and increasingly for a long period of time up to the life of the patient. There is also mounting evidence that the sensing solution in these efforts will involve increasingly larger numbers of electrode contacts which are often placed in a dense arrangement. Baker M: *From promising to practical: tools to study networks of neurons*. Nature Methods, 7(11):877-883, 2010. Rubehn B, Bosman C, Oostenveld R, et al.: *A MEMS-based flexible multichannel ECoG-electrode array*. Journal of Neural Engineering, 6(3):109-118, 2009.

The currently available as well as the proposed solutions for continuous real-time sensing of the electrical activity of the brain are all intolerant to faults. Lanning B, Joshi B, Kyriakides T, Spencer D, Zaveri H: *Emerging technologies for brain implantable devices. Epilepsy: The Intersection of Neurosciences, Biology, Mathematics, Physics and Engineering*, 2011. Edited by: Osorio I, Zaveri H P, Frei M G, Arthurs S. CRC Press. There are several aspects of an implantable sensing device which can fail. These include the reference electrode, sensors, signal conditioning and digitization circuitry, and computation, power and communication sub-systems. Faults which affect sensing can arise because of sensor failure due to mechanical stress on the sensor or the connecting wires during surgery to place electrodes or due to stress from changes in the brain and the surrounding milieu thereafter. Sensor failure can also arise because the foreign body response of the brain can result in encapsulation of a sensor due to gliosis. In case of erroneous behavior of the implanted sensors, the electrical activity at the site of the failed electrode contact will not be observed correctly, thereby impairing the purpose of the implanted device. For epilepsy surgery this may require the approximation of information from neighboring sensors if they exist. In the case of a seizure control device the failure of error free monitoring of the electrical activity of the brain may necessitate surgery to remove faulty sensors and implantation of a new set of sensors. While the initial surgery to place sensors carries a risk, surgery to replace sensors and a device can involve further risk with associated morbidity and mortality which remain to be determined but is expected to be equal to or greater than that of the surgery to place the first set of sensors.

It is the inventors' belief that reliable sensing of the human brain for an extended period of time necessitates fault-tolerant multielectrode array design to assure multielectrode array reliability. That is, fault-tolerance must be incorporated into the device architecture. Accordingly, the present invention provides two hardware redundancy based fault-tolerant solutions to manage intermittent and permanent faults. A permanent fault is one which exists indefinitely in absence of a corrective action while an intermittent fault is one which appears and disappears repeatedly.

The present invention overcomes the deficiencies of prior systems, method and apparatuses by providing a brain implantable device composed of one or more multielectrode sensing arrays with fault-tolerant mechanisms. Two different embodiments are disclosed in accordance with the present invention for the provision of such a multielectrode array. The first embodiment is composed of rows or columns of spare sensor modules on the edge of or within the sensor grid of the multielectrode array. In accordance with the second embodiment, spare sensor modules in the multielectrode array are based on a defined geometry (interstitial redundancy). A reconfiguration solution is provided for both the spare row or column and the interstitial redundancy solutions. Finally, the efficacy of the present solutions is demonstrated through analytical and simulation determinations of the reliability of multielectrode arrays designed with row or column or interstitial redundancy.

SUMMARY OF THE INVENTION

The present invention comprises a method and device to monitor and intervene in the neurological biosignaling of human patients suffering from disorders such as epilepsy. In one aspect, the present invention includes multiple implanted sensors placed within a sensor network using a scalable design to accommodate future increases in numbers of sensors. The present invention uses hierarchical hardware redundancy based fault-tolerant design to accommodate failure of sensors.

It is, therefore, an object of the present invention to provide a multielectrode array with fault-tolerance for use in conjunction with a brain implantable device. The multielectrode array includes a sensor grid composed of a plurality of sensors, the plurality of sensors including primary sensors and spare sensors. The multielectrode array also includes signal processing circuitry associated with the plurality of sensors and a control system associated with the sensor grid for replacing faulty primary sensors with spare sensors.

It is also an object of the present invention to provide a multielectrode array wherein each of the primary sensors is linked to an amplifier to define a primary sensor module and each of the spare sensors is linked to an amplifier to define a spare sensor module.

It is another object of the present invention to provide a multielectrode array wherein the control system replaces faulty primary sensor modules with spare sensors modules.

It is a further object of the present invention to provide a multielectrode array wherein the signal processing circuitry includes a primary A/D converter and a spare A/D converter.

It is also an object of the present invention to provide a multielectrode array wherein fault-tolerance is based upon redundancy.

It is another object of the present invention to provide a multielectrode array wherein fault-tolerance is based upon interstitial redundancy.

It is a further object of the present invention to provide a multielectrode array wherein the multielectrode array includes n rows and m columns of primary sensors, and s columns or rows of spare sensor modules.

It is also an object of the present invention to provide a multielectrode array wherein the s columns or rows of spare sensor modules are on an edge of the multielectrode array or within the multielectrode array.

It is another object of the present invention to provide a multielectrode array wherein the multielectrode array includes a (m, n) structure of sensors where m is the number of rows and n is the number of columns of primary sensors and spare sensors are placed in interstitial sites between the primary sensors.

It is a further object of the present invention to provide a multielectrode array wherein reconfiguration of the sensors is achieved by a graph matching approach.

It is also an object of the present invention to provide a brain implantable device for control of epilepsy including a multielectrode array with fault-tolerance including a sensor grid composed of a plurality of sensors. The plurality of sensors includes primary sensors and spare sensors. The multielectrode array also includes signal processing circuitry associated with the plurality of sensors and a control system associated with the sensor grid for replacing faulty primary sensors with spare sensors. The brain implantable device also includes external circuitry associated with the multielectrode array for receiving EEG signals generated by the multielectrode array.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 5(a) is example of (4, 4) interstitial redundancy array with spare modules (black) at the interstitial sites of the primary modules (gray), and FIG. 5(b) shows corresponding graph model for the (4, 4) interstitial redundancy array shown in FIG. 5(a) where each node in the graph represents a primary or spare module. Note, in the graph representation each primary module is connected to the spare modules which can replace it, and each spare module is connected to the primary modules it can replace.

DESCRIPTION OF THE PREFERRED EMBODIMENTS

Figure 1:
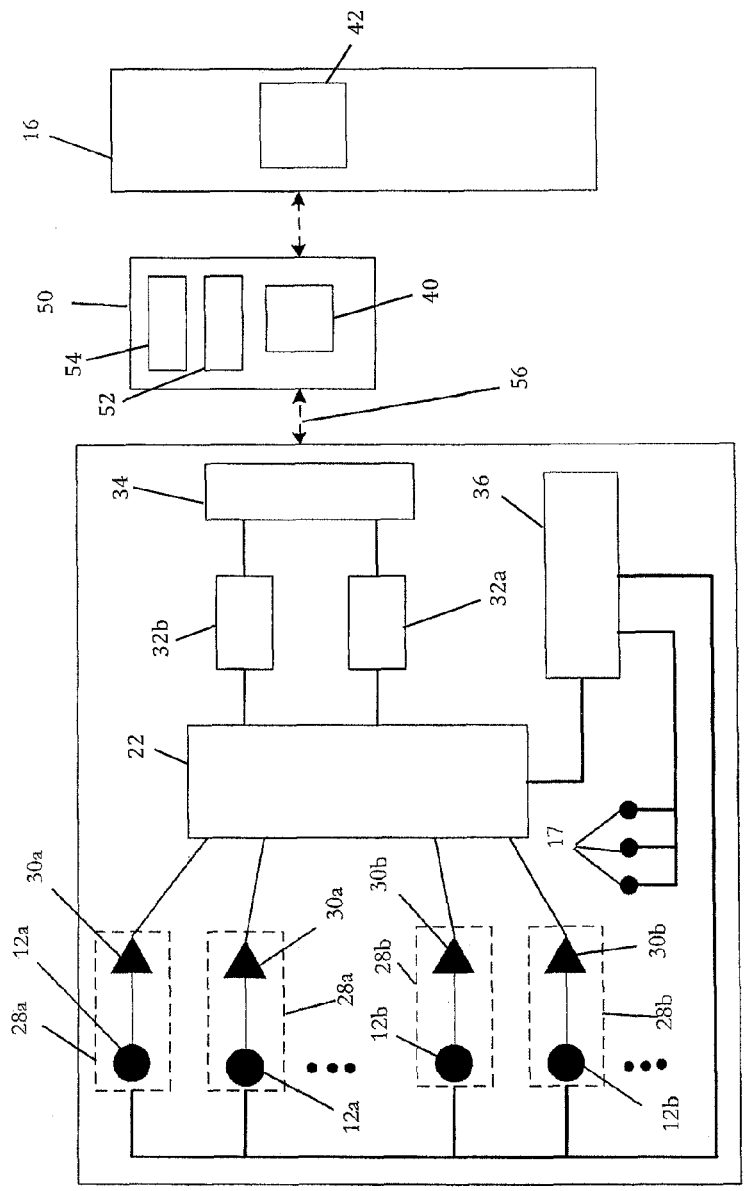
FIG. 1 is a block diagram of the present brain implantable device including an intracranial electrode/sensor unit, subcutaneous central processing node and an external system.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

With the use of electronic devices in the treatment of the epilepsy it is our belief that the reliable sensing of the human brain for an extended period of time necessitates fault-tolerant design to assure system reliability. As will be appreciated based upon the following disclosure, fault-tolerance can be decomposed into two parts: fault detection and reconfiguration. The present invention provides fault-tolerant approaches for intermittent and permanent faults that might occur in the implementation of electronic systems in the diagnosis and treatment of epilepsy.

It is appreciated, fault-tolerant operation can be defined as the process by which a system continues to perform its specified tasks correctly even in the presence of faults. The goal of fault-tolerant design is to improve system dependability which is defined as the ability of a system to deliver a service at an acceptable level of confidence. Dependability is most commonly characterized in terms of the attributes of reliability and availability. Koren I, Krishna C M: *Fault-tolerant Systems*. San Francisco: Morgan Kaufmann, 2007. A fault-tolerance solution requires the use of redundancy. The amount of redundancy can be quantified by the redundancy ratio. We define reliability, availability, and redundancy ratio below. It will be appreciated the reliability of a system is the conditional probability that the system performs its tasks correctly during a time interval $[t_0, t]$, given that the system was performing them correctly at time to. Further, the availability of a system is the probability that the system is available to perform its tasks correctly at time t. Finally, the redundancy ratio is the ratio of the number of spare modules to the number of primary modules.

I. Brain Implantable Device

In accordance with a preferred embodiment, the present invention provides a brain implantable device 10 to control seizures. We believe seizure occurrence is a function of susceptibility which arises due to an interaction between patient state, cortical and subcortical tone, and aberrant brain connectivity. The present invention employs an approach that starts by identifying known factors that influence the probability of seizure occurrence, refines the definition and characteristics of those factors, and then combines them in a weighted fashion to create a multivariate predictor. The different aspects that inform this approach include sensing of the brain, the effect of patient state on seizures, effect of antiepileptic drugs (AEDs) on cortical and subcortical tone, and aberrant brain connectivity.

The present brain implantable device 10 is modular and scalable, and composed of one or more units placed intracranially to target different areas of the brain. Using currently available processing technology and processing technology developed in the future, the present brain implantable device 10 continuously monitors the patient's state and vulnerability to seizure and intervenes to block the development of seizures by preventing the vulnerable region of the brain from entering states which lead to seizure, or in the event that a seizure is underway intervenes to terminate it. It is appreciated the intervention attempting to prevent seizures may occur through electrical stimulation, local delivery of drugs by a brain implantable drug delivery device or local cooling of the brain. As such, and despite the present disclosure of an electrical stimulation based system, it is appreciated various intervention techniques may be possible within the spirit of the present invention. As will be explained below in detail, the present brain implantable device 10 incorporates fault-tolerance at multiple levels, and communicates with an external device 16 to interface to the external world and facilitate the use of new algorithms to sense vulnerable states leading towards seizure and transfer control parameters and data.

Figure 2:
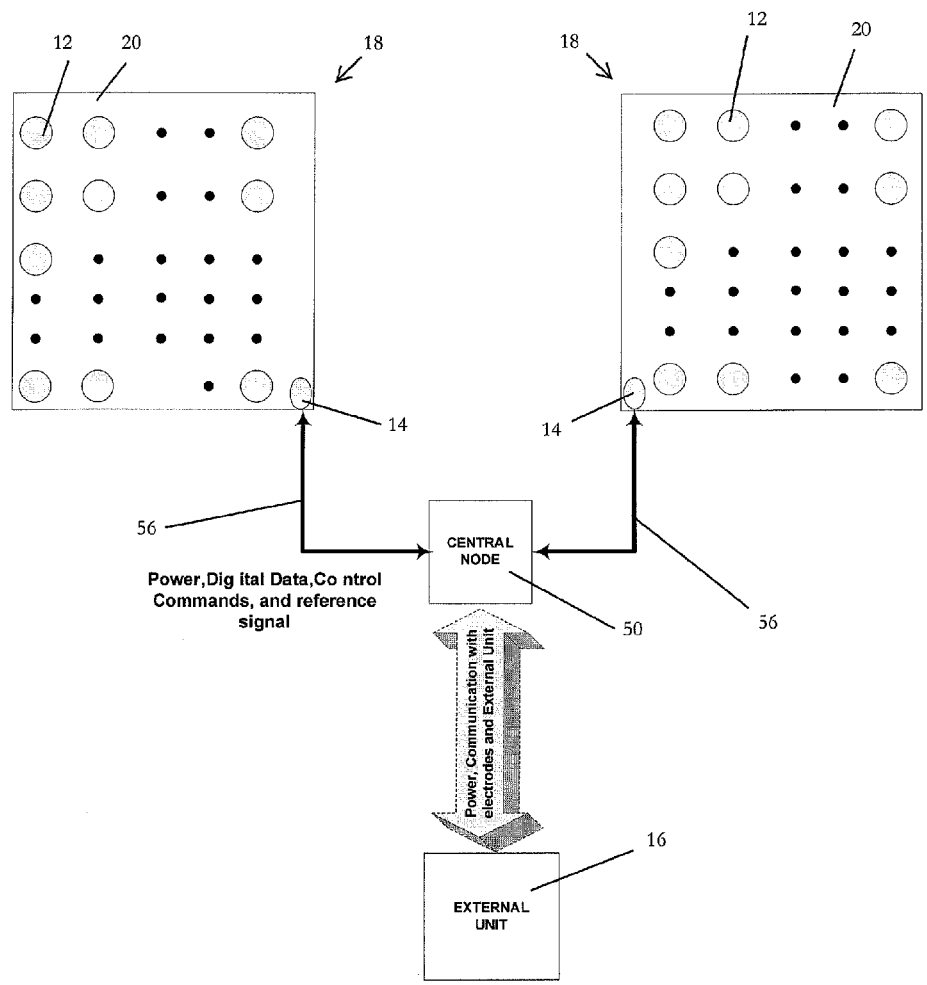
FIG. 2 is a schematic of the present brain implantable device with two multielectrode arrays and a central node. An external unit and the data, power, and communication paths are also shown.

Referring now to FIGS. 1 and 2, a block diagram and schematic, respectively, of the brain implantable device 10 are disclosed. The brain implantable device 10 provides for sensing the brain with an adaptable, distributed, network of sensors 12 forming part of a multielectrode array 18. In accordance with a disclosed embodiment as shown with reference to FIG. 1, multielectrode array 18 includes a plurality of networked sensors 12 and signal processing circuitry 14 in communication with the previously mentioned external system 16. It is appreciated, the signal processing circuitry 14, external system 16, reference electrodes 17, and other standard components of the brain implantable device 10 may be implemented using various known techniques and are therefore not addressed in detail in the present disclosure.

A block diagram of one embodiment of the brain implantable device 10, with its associated external system 16, of the present invention is presented in FIG. 2. As a non-limiting example: the sensor network includes two sensor grids 20 each composed of a plurality of sensors 12 in a manner discussed below in greater detail. The two sensor grids 20 are connected to a signal processing circuitry 14 in the form of network of analog switches (for example, analog multiplexer 22), amplifiers 30a, 30b, A/D (analog-to-digital) converters 32a, 32b, etc. to amplify, condition, and digitize the signals. As discussed above, the signal processing disclosed in commonly owned U.S. Pat. No. 8,165,684 (U.S. patent application Ser. No. 12/184,663), entitled "WIRELESS SYSTEM FOR EPILEPSY MONITORING AND MEASUREMENT", issued Apr. 24, 2012, and U.S. patent application Ser. No. 13/429,109, entitled "WIRELESS SYSTEM FOR EPILEPSY MONITORING AND MEASUREMENT", filed Mar. 23, 2012, which are incorporated herein by reference, may also be employed for conditioning, amplifying, filtering, and digitizing multi-channel brain activity in an implantable device and transmitting this activity wirelessly. The digital signals will be analyzed and appropriate intervention signals will be generated by the internal chip control system 36 of the multielectrode array 18, the central processing node 50 positioned between the multielectrode array 18 and the external system 16, or processing systems of the external system 16. More particularly, and in accordance with the disclosed embodiment, each of the sensor grids 20 form part of a multielectrode array 18 as disclosed herein. Further, and as will be appreciated based upon the following disclosure, each grid of sensors 20 is composed of a plurality of primary sensors 12a and a plurality of spare sensors 12b for fault-tolerance. Further, multiple, selectable, reference electrodes 17 will be available for fault tolerance.

Although a preferred system as described above is disclosed, various architectures may be employed. For example, and in accordance with a first alternate embodiment, the signal processing circuitry may take the form where the output of the bioinstrumentation amplifiers is digitized by A/D convertors, which are dedicated so there is one A/D converter per signal stream, and converted by a digital multiplexer into a parallel data stream which is converted to a serial data stream by the parallel to serial convertor. In this case a digital switching circuit can be employed to select the input into the digital multiplexer. In another example (that is, a second alternate embodiment), the circuitry may consist of an analog switch to select the output of primary or spare sensors and conduct the selected analog signals out of the multielectrode array. It is appreciated that there may be a tradeoff between the alternate embodiment and the disclosed embodiment of FIG. 1, in that component count and power consumption may be lower in the disclosed embodiment of FIG. 1. The second alternate embodiment describes an extension of the current passive electrode grids, which have an analog output, to fault tolerance.

The goal of fault-tolerance is to improve system dependability which is defined as the ability of a system to deliver service at an acceptable level of confidence. The concepts are applied in accordance with the present invention to provide a fault-tolerant multielectrode array 18.

Referring to FIG. 1, the architecture of the present brain implantable device 10 is composed of a multielectrode array 18 with multiple contacts (sensors) 12a, 12b and signal processing circuitry 14 to condition and digitize the sensed signals. Each primary sensor 12a and spare sensor 12b in the sensor grid 20 is connected, through a switching network in the form of an analog multiplexer 22, to signal processing circuitry (in accordance with a preferred embodiment, signal conditioning and digitizing circuitry) 14. The signal processing circuitry 14 includes amplifiers 30a, 30b, one or more filters as needed (not shown), an A/D converter 32a, 32b, a D/A converter (if one is needed), and parallel/serial converter 34, all under the control of an internal chip control system 36.

In accordance with a preferred embodiment, each sensor 12a, 12b and its associated amplifier 30a, 30b is defined as a sensor module 28a, 28b. As such, and in accordance with the present invention, a fault-tolerant approach based on hardware redundancy is provided wherein faulty primary sensor modules 28a are detected and isolated, and the multielectrode array 18 is then reconfigured so as to replace the faulty primary sensor module 28a with a healthy spare sensor module 28b. While the present disclosure focuses upon the replacement of faulty primary sensor modules with healthy spare sensor modules, it is appreciated the present system also identifies faulty spare sensor modules.

More particularly, and with reference to FIG. 1, the multielectrode array 18 includes primary and spare sensor modules 28a, 28b (that is, a sensor 12a, 12b and its associated amplifier 30a, 30b) associated in with the electronic signal processing circuitry 14. The electronic signal processing circuitry 14 is composed of analog switches in the form of an analog multiplexer 22, A/D converters 32a, 32b, a parallel/serial converter 34 and an internal chip control system 36. The amplified signals of the amplifiers 30a, 30b are processed by the analog multiplexer 22 which transmits the processed signals to either the primary A/D converter 32a or the spare A/D converter 32b, which then transmitted the digital signal to the parallel/serial converter 34. All of the operating components of the multielectrode array 18 are controlled by the internal chip control system 36. As indicated in FIGS. 1 and 2, each multielectrode array 18 can be used stand-alone or in conjunction with other multielectrode arrays 18 as a distributed network of multielectrode arrays which are connected (via wired electrical lines 56) to a central node 50. The central node 50 contains computation (or microprocessor) 54, power 52 and communication 40 subunits. It can be appreciated that multiple such central nodes 50 with connected multielectrode arrays 18 can be implanted in a single patient if necessary. As shown in FIGS. 1 and 2, the central node 50 provides the various connected multielectrode arrays 18 with power 52 under the control of a microprocessor 54 maintained by the central node 50.

Following the network of sensors 12a, 12b, a switching network on the multielectrode array 18 connects sensors to the input of neural recording amplifiers. Digitally controlled, variable voltage gain can be used along with the important removal of circuit and contact DC offsets. The neural recording amplifiers are followed by analog-to-digital converter(s) to digitize the neural signals for later routing and processing of the sensed signals. In addition to routing electrode contacts to neural recording amplifiers, the switching network can also disconnect the amplifier inputs and connect stimulation voltages across the sensors for neural intervention.

It is important to note the present brain implantable device can also employ wireless coupling for the transmission of power and data between the external system 16 and the central node 50, in particular, the power supply 52 of the central node 50. This is achieved through the utilization of complimentary IR/RF transceivers 40, 42 on both the central node 50 and the external system 16. This is shown in FIG. 1 for the central node 50 and the external system 16, and is implemented in a manner similar to that disclosed in commonly owned U.S. Pat. No. 8,165,684 (U.S. patent application Ser. No. 12/184,663), entitled "WIRELESS SYSTEM FOR EPILEPSY MONITORING AND MEASUREMENT", issued Apr. 24, 2012, and U.S. patent application Ser. No. 13/429, 109, entitled "WIRELESS SYSTEM FOR EPILEPSY MONITORING AND MEASUREMENT", filed Mar. 23, 2012, which are incorporated herein by reference.

The present brain implantable device 10 provides for multimodal intracranial EEG monitoring and intervention, and can be powered remotely through an RF link and transmits data and control signals through a high bandwidth IR link (16 Mbits/sec). It is also appreciated a multimodal electrode may be developed to allow us to more fully measure brain activity within the seizure onset area in patients. The multimodal electrode will be an enhancement of the existing Spencer depth electrode to allow recording of intracranial EEG, pH and potassium ([K+]). Each sensor, which could be part of a large, addressable (multiplexed) array, will transduce the electrical signal (induced surface charge) from the biological parameter of interest (i.e., ions such as hydrogen (pH) or potassium, and intracranial EEG) into a direct electrical readout.

II. Fault-Tolerant Multielectrode Array

As discussed above, the present implantable device 10 includes a multielectrode array 18 with multiple electrode contacts (sensors) 12a, 12b, forming a sensor grid 20, and signal processing circuitry 14 to condition and digitize the sensed signals. As discussed above, each sensor 12a, 12b in the sensor grid 20 is connected to signal conditioning and processing circuitry 14 which includes an amplifier 30a, 30b, an A/D converter 32 and a parallel/serial converter 34. For simplicity we consider a modular design, where a sensor 12a, 12b and its accompanying amplifier 30a, 30b are considered to be a sensor module 28a, 28b. However, it is appreciated other implementations are certainly possible without departing from the spirit of the present invention. This circuitry may be connected to additional sensor modules for computation, communication and intervention.

In accordance with the present invention, two fault-tolerant solutions based on hardware redundancy are disclosed. The fault-tolerant solutions of the present invention seek to detect and locate a faulty primary sensor module 28a and reconfigure the multielectrode array 18 after isolating and replacing the faulty sensor module 28a with a working spare sensor module 28b.

It should be appreciated that "fault detection" as used herein is the process of by which it is recognized that a fault has occurred; "fault location" is the process of determining where the fault has occurred; and "reconfiguration" is the process of isolating a faulty component from the remainder of the system and restoring the system performance to an acceptable level of operation.

A. Spare Row or Column of Modules

Figure 3:
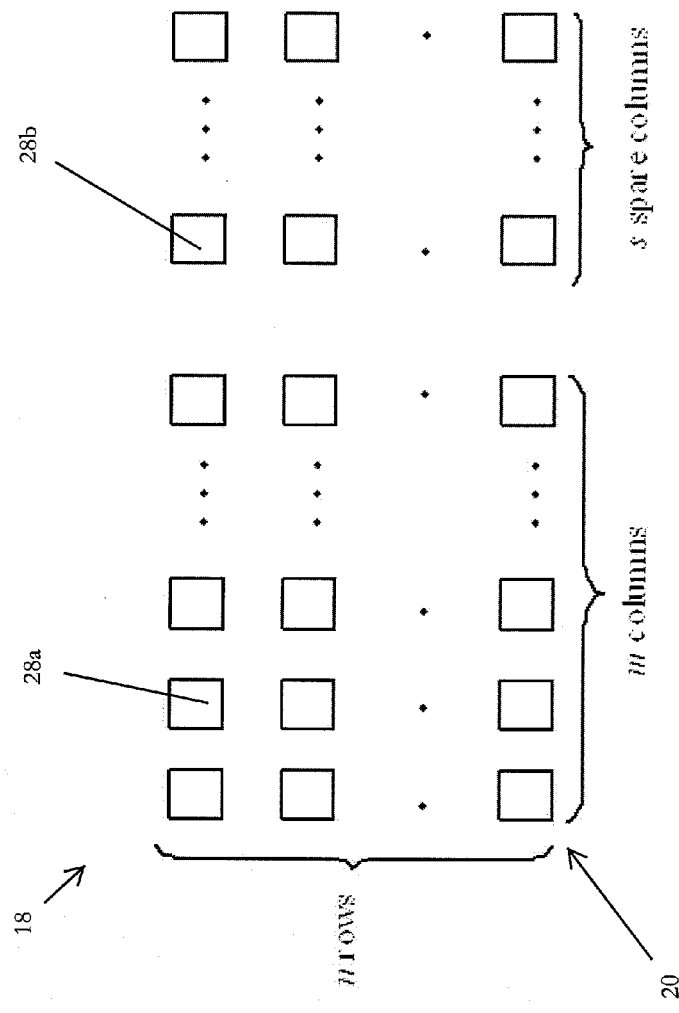
FIG. 3 is an n×m array of primary modules with s columns of spare modules placed to the right of the array of primary modules.

For purposes of understanding and describing the present multielectrode array 18, and with reference to FIG. 3, it is assumed the implanted multielectrode array 18 includes n rows and m columns of primary sensor modules 28a. In accordance with the first fault-tolerant solution of the present invention, s columns of spare sensor modules 28b in addition to the primary sensor modules 28a are incorporated in to the multielectrode array 18. The spare columns or rows of spare sensor modules 28b can be located at the edge of the multielectrode array 18 or within the multielectrode array 18. For the simplicity of exposition it shall be assumed the spare columns of spare sensor modules 28b are located at the right edge and spare rows of spare sensor modules 28b, if included in the design, are located at the bottom edge of the multielectrode array 18. Once a faulty primary sensor module 28a is identified, a reconfiguration process is initiated in which the faulty primary sensor module 28a is replaced by its nearest fault-free spare sensor module 28b neighbor on the right. This switching is achieved under the control of the internal chip control system 36 of the multielectrode array 18.

To evaluate the reliability of the fault-tolerant multielectrode array 18 it is assumed, the failure rate, that is failures per unit time, is considered to be a constant value, $\lambda$. Under this assumption it can be shown that the reliability $R_m(t)$ of each primary sensor module 28b is given by (1):

$$R_m(t) = e^{-\lambda t} \quad (1)$$

This exponential relationship between sensor module reliability and time is known as the exponential failure law. It states that when the failure rate function is a constant, reliability is proportional to a decaying exponential as a function of time. If the multielectrode array 18 can tolerate r failed sensor modules, for the (m+s) sensor modules in each row, where (r<m+s), then the reliability of each row of sensor modules is given by (2):

$$R_{row}(t) = \sum_{i=0}^{r} \binom{m+s}{i} R^{m+s-i}(t)(1-R(t))^i \quad (2)$$

where, $$\binom{m+s}{i} = \frac{(m+s)!}{(m+s-i)!i!}$$

In this disclosure it is assumed the sensor module failures occur independently.

If k rows have to be operational, where k≤n, then the reliability of the multielectrode array 18 is given by (3):

$$R(t) = \sum_{j=0}^{n-k} \binom{n}{j} R_{row}^{n-j}(t)(1-R_{row}(t))^j C \quad (3)$$

where 'C' is the fault coverage. As used herein, "fault coverage" is a measure of the system's ability to recover from faults and continue to operate correctly. It is expressed as the probability that the system recovers from the fault given the existence of the fault.

Figure 4:
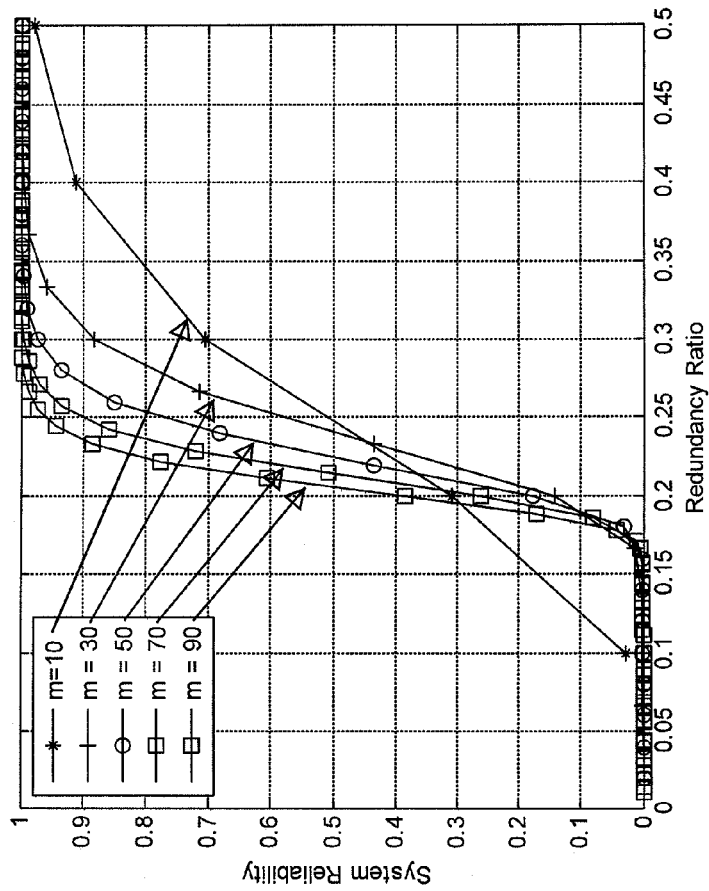
FIG. 4 shows reliability as a function of redundancy ratio for a fault-tolerant multielectrode array (MEA) solution which includes spare columns. Here the number of rows, n=100, fault coverage C=1, k=n, and module reliability is assumed to be 0.9.

As an example, we demonstrate through computer based simulation the performance of the proposed first solution for a multielectrode array 18 with the number of rows of primary and spare sensor modules 28a, 28b fixed at 100 and fault coverage C=1. In this evaluation sensor module reliability was assumed to be 0.9 (i.e., the probability that the primary sensor module is functioning in the time interval [$t_0$, t]), and k=n, i.e. all the rows had to be operational. FIG. 4 shows the reliability of multielectrode array 18 with the number of columns ranging from 10 to 90 and redundancy ratio ranging between 0 and 0.5. A higher redundancy ratio implies that a higher percentage of sensor modules in the multielectrode array 18 are spares sensor modules 28b. For example, a redundancy ratio of 1 implies there is a spare sensor module 28b for each primary sensor module 28a. We observe, the reliability increases for a given redundancy ratio with increasing non-spare columns. This suggests that with this solution it is possible to create a highly reliable multielectrode array 18 using a lower percentage of spare sensor modules 28b.

Although spare columns of spare sensor modules 28b are used in the solution disclosed above, it is appreciated the method can be modified to incorporate both spare columns of spare sensor modules and spare rows of spare sensor modules. While the reconfiguration scheme is systematic, i.e. a faulty sensor module 28a is replaced by the nearest fault-free sensor module 28b to its right (or below if spare rows of spare sensor modules are used), the reconfiguration process may involve reconfiguration of several fault-free primary sensor modules at the same time. This is because whenever a faulty sensor module 28a is located the entire row or column of primary sensor modules which includes the faulty primary sensor module 28a will be replaced. This increases the hardware overhead.

In order to address this inefficiency, a second fault redundancy solution, known as interstitial redundancy, is proposed below. The second fault redundancy solution attempts to reconfigure a faulty multielectrode array 18 without reconfiguration of fault-free primary sensor modules 28b.

B. Interstitial Redundancy

FIG. 5(a) shows a (m, n) multielectrode array 18 structure of sensor modules where m is the number of rows and n is the number of columns of primary nodes of primary sensor modules 28a. In this depiction, a sensor module is either primary sensor module (gray) 28a or spare sensor module (black) 28b with spare sensor modules 28b being placed in interstitial sites between primary sensor modules 28a. For the purposes of the present disclosure, such a fault-tolerant multielectrode array 18 architecture is called an (s, p) interstitial redundancy array (IRA). In a (s, p) interstitial redundancy array, each non-boundary primary sensor module 28a can be replaced by one of s spare sensor modules 28b and each non-boundary spare sensor module 28b can serve as a spare for p primary sensor modules 28a.

Interstitial redundancy arrays can have a different degree of redundancy depending on the number and location of spare sensor modules 28b. In this disclosure we present several example multielectrode arrays with interstitial redundancy, their corresponding graph models, and the performance of the fault tolerant solution. These multielectrode arrays have a wide range of degree of redundancy. For example, consider the (4, 4) interstitial redundancy array shown in FIG. 5(a) where each non-boundary primary sensor module 28a can be replaced by any one of the four available spare sensor modules 28b adjacent to it, and each spare sensor module 28b is available to its four neighboring primary sensor modules 28a. Furthermore, each of the four corner primary sensor modules 28a can be replaced by one spare sensor module 28b and the remaining boundary primary sensor modules 28a can be replaced by one of two spare sensor modules 28b. This relationship can be effectively captured by a graph model for this interstitial redundancy array. FIG. 5(b) shows the graph model of the (4, 4) interstitial redundancy array shown in FIG. 5(a). As before, gray nodes in the graph represent primary sensor modules 28a while black nodes represent spare sensor modules 28b. If a spare sensor module 28b (or gray node) can replace a primary sensor module 28a (or black node), then there is an edge between the two nodes in the graph. It can be observed that no two gray nodes are neighbors in the graph since a primary sensor module 28a cannot replace another primary sensor module 28a.

It should be appreciated an undirected graph G(V, E) is a structure which consists of a set of vertices V={$v_1$, $v_2$, ... } and a set of edges E={$e_1$, $e_2$, ... } where each edge e is incident to the elements of an unordered pair of vertices (u, v) which are not necessarily distinct.

III. Reconfiguration of Interstitial Redundancy Arrays

When a faulty primary sensor module 28a is identified, a reconfiguration process is initiated and the detected faulty primary sensor module 28a is replaced by an available fault-free spare sensor module 28b. The reconfiguration strategy is described in detail in this section. Unlike the first fault-tolerant solution where the spare sensor modules 28b were placed in rows or columns within or on the boundary of the multielectrode array 18, interstitial redundancy places spare sensor modules 28b in interstitial spaces of the multielectrode array 18. This allows the use of a local approach to simplify multielectrode array 18 reconfiguration in the presence of faults. As will be discussed below, the reconfiguration scheme is based on a graph theoretic approach.

A. Maximum Matching Algorithm

The replacement of a faulty primary sensor module 28a by a spare sensor module 28b can be performed in an optimum manner by a maximum matching algorithm from graph theory. Even S: *Graph Algorithms*. Computer Science Press, 1979. We illustrate this through an example. Consider, for example the (4, 4) interstitial redundancy array and its graph model shown in FIGS. 6(a) and 6(b), respectively. This is a 5×5 multielectrode array 18 with 16 spare sensor modules 28b arranged in a 4×4 array. Four of the primary sensor modules 28a are faulty and none of the spare sensor modules 28b is faulty.

Given definition "A" that an undirected graph G=(V, E), a matching is a subset of edges M⊆E such that for all vertices v∈V, at most one edge of M is incident on v. A vertex v is matched by matching M if some edge in M is incident on v; otherwise v is unmatched. An edge e is a free edge if and only if $$e \notin M.$$

Further, a maximum matching is a matching of maximum cardinality, that is, a matching M such that for any matching M' (that is, definition "B"), $$|M| \geq |M'|.$$

Figures 6A, 6B:
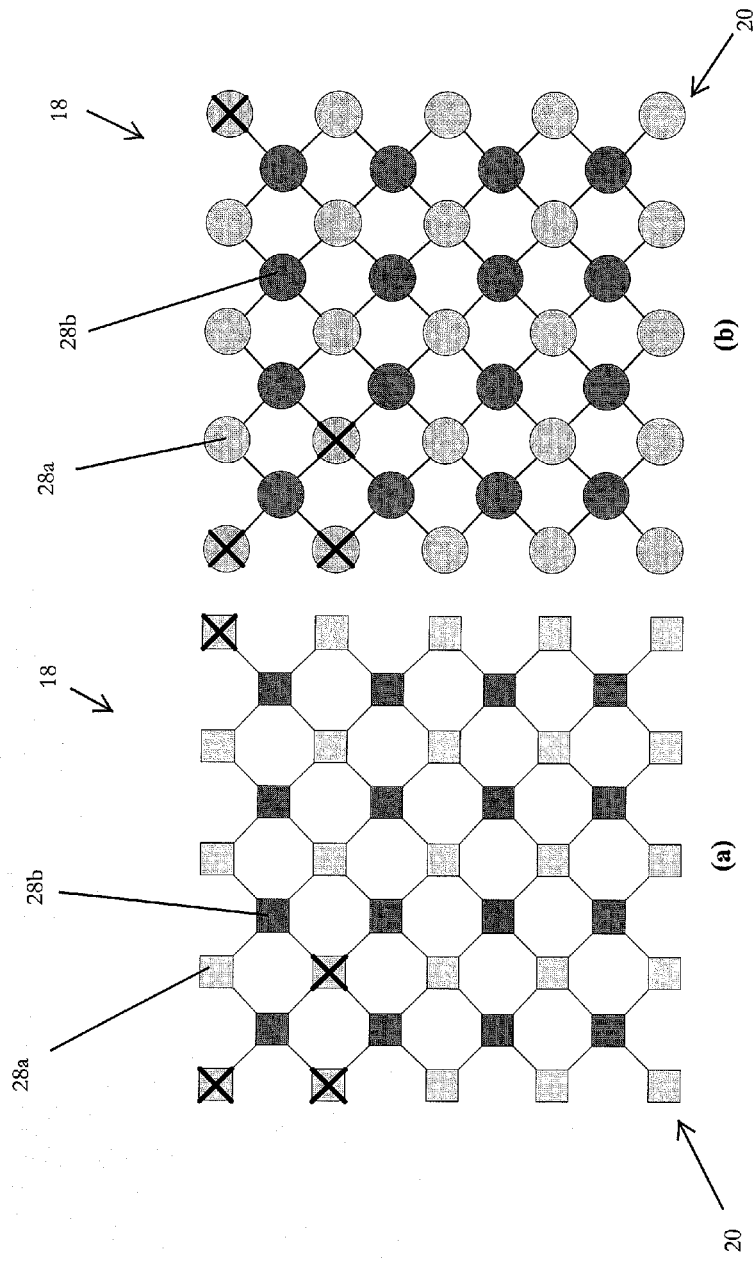
FIG. 6(a) is a (4, 4) interstitial redundancy array with an example set of faults. Here, primary modules (1, 1), (2, 1), (2, 2) and (1, 5) are faulty.
FIG. 6(b) shows the corresponding graph model for the (4, 4) interstitial redundancy array shown in FIG. 6(a). A faulty module is marked with an 'X'.

From the graph model of an interstitial redundancy array (FIG. 6(b)) a subgraph can be constructed composed of nodes corresponding to faulty primary sensor modules 28a and spare sensor modules 28b that can potentially replace these faulty nodes. In this subgraph, an edge between a primary node representing a primary sensor module 28a and a fault-free spare node representing a spare sensor module 28b exists if and only if the spare sensor module 28b can replace the primary sensor module 28a. It can be observed that this graph is a bipartite graph since no two primary nodes and no two spare nodes are adjacent (FIG. 7(a)). It is appreciated that a bipartite graph is a graph in which V=X∪Y and X∩Y=Ø and each edge has one end vertex in X and one in Y.

For a given set of faulty primary sensor modules 28a, we can construct the bipartite graph of the interstitial redundancy array with the vertex set partition {X,Y}, and the edge set E, where X is the set of faulty primary nodes representing primary sensor modules 28a and Y is the set of all the neighboring fault-free spare nodes representing spare sensor modules 28b. Note, that in such a bipartite graph, any pair of matched vertices incident on an edge e, e∈M will consist of one faulty primary sensor module 28a and one spare sensor module 28b such that the spare sensor module 28b corresponding to the matched node can replace the corresponding faulty primary sensor module 28a. It is evident from definitions "A" and "B" above that the maximum matching involves finding δ, the maximum number of mutually disjoint edges in E, such that, no two edges share the same node, implying that a spare sensor module 28b can replace no more than one primary sensor module 28a at any given time and a given faulty primary sensor module 28a cannot be replaced by more than one spare sensor module 28b.

We are interested in determining if δ=|X| that is, whether every faulty primary sensor module 28a can be replaced by a fault-free spare sensor module 28b.

A maximum matching for a bipartite graph can be obtained using any method that is based on the following theorem.
Theorem 1: The number of edges in a maximum matching of a bipartite graph G is equal to the maximum flow, F, in its corresponding network, N(G). Even S: *Graph Algorithms*. Computer Science Press, 1979.

The key idea here is to construct a network N(G) whose directed graph is as defined in equations (4) and (5):

$$\overline{V} = \{s, t\} \cup V, \tag{4}$$

And $$\overline{E} = \{s \rightarrow u | x \in X\} \cup \{y \rightarrow t | y \in Y\} \cup \{x \rightarrow y | x - y \text{ in } G\}. \tag{5}$$

An edge is connected from node s to every node x, x∈X. Similarly, an edge from every node y, y∈Y connects to node t.

Figures 7A, 7B:
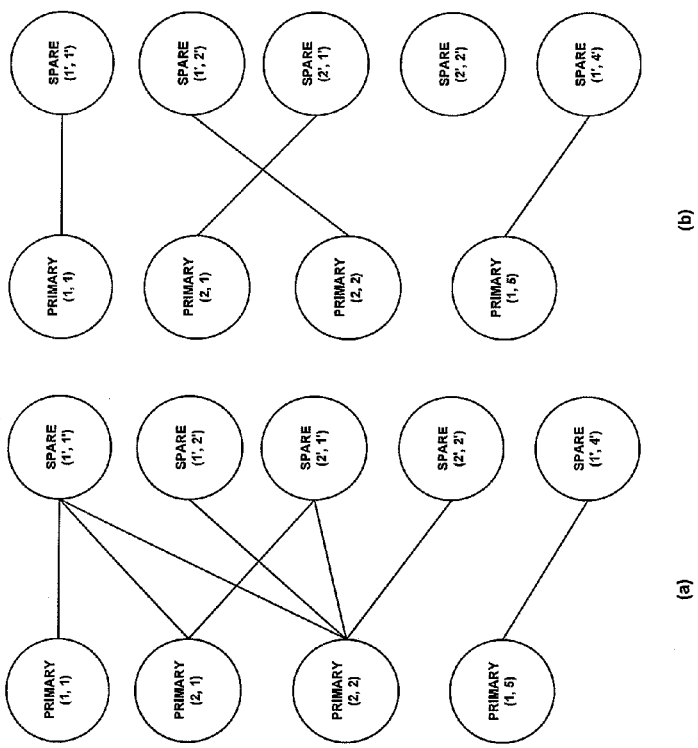
FIG. 7(a) is a subgraph of the four faulty modules shown in FIG. 6(a), and all the spare modules which can replace them. This sub-graph is a bipartite graph.
FIG. 7(b) shows a maximum matching solution of the bipartite graph shown in FIG. 7(a). This matching is one possible mapping of faulty primary modules to spare modules to correct the faults in the multielectrode array shown in FIG. 6(a).

As an example, consider the (4, 4) interstitial redundancy array with four faulty primary sensor modules 28a (see FIG. 6(a)). The corresponding graph model is shown in FIG. 6(b). Bipartite graphs for the sub-graph containing the faulty primary nodes and connected spare nodes are shown in FIG. 7(a) and FIG. 7(b). The directed graph of the network N(G) is shown in FIG. 8.

Figure 8:
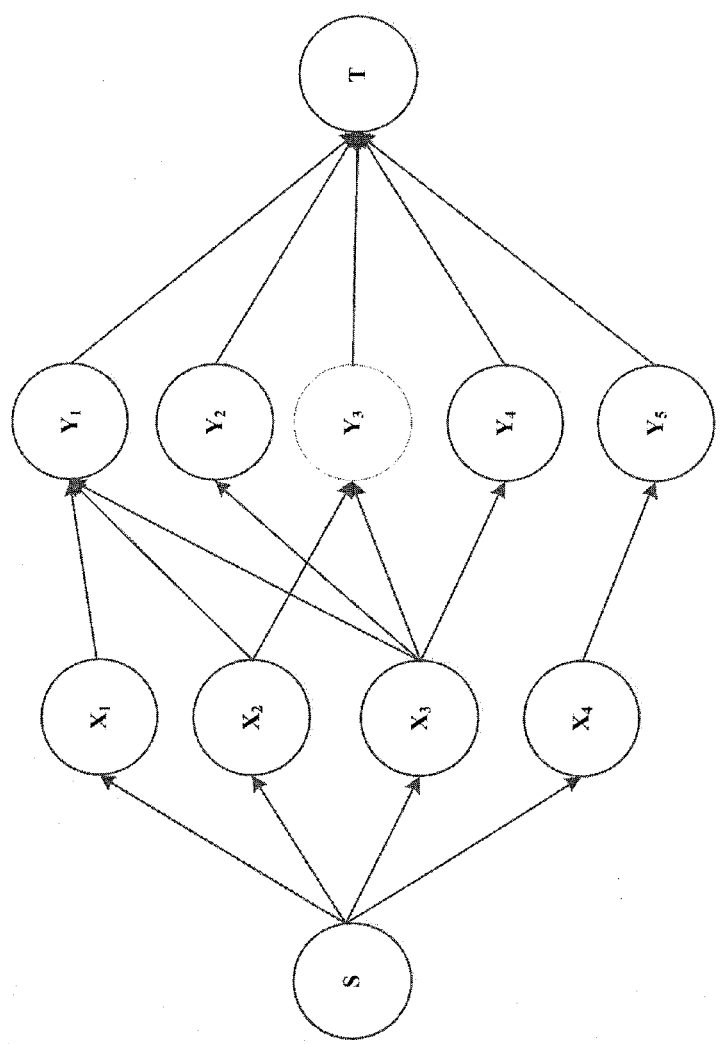
FIG. 8 is a directed graph of the network of the bipartite graph in FIG. 7(a).

Any algorithm for maximum flow can be applied to the directed bipartite graph in FIG. 8 to determine the maximum flow from s to t. Papadimitriou C H, Stieglitz K: *Combinatorial Optimization, Algorithms and Complexity*. Englewood Cliffs, N.J.: Prentice-Hall, 1982. From Theorem 1 the maximum flow will give the maximum matching. For example, Dinic's algorithm for maximum flow, which runs in O(√V E) when applied to the directed graph of FIG. 8 leads to the maximum matching graph shown in FIG. 7(b). The application of the maximum flow algorithm during the reconfiguration process will identify an optimum solution to replace faulty primary nodes by matching a maximum number of faulty primary nodes with available spare nodes.

B. Reconfiguration Procedure

As discussed below in greater detail, fault-identifying procedures are used to continuously examine both primary and replacement spare (once they are in use) sensor module 28a, 28b performance to detect a fault. Once a fault is detected, a second algorithm may be used, if necessary, to locate the faulty sensor module. These algorithms can run on the internal chip control system 36 embedded in the multielectrode array 18, the microprocessor 54 of the central node 50, or on an external computer which can communicate with the multielectrode array 18. The location of a fault triggers the reconfiguration process wherein the faulty primary sensor module 28a is disconnected and replaced with a healthy and available spare sensor module 28b. This switching is preferably achieved using an analog switch and may also be performed using an analog multiplexer in a manner well known to those skilled in the art.

IV. Reliabilty Analysis of Interstitial Redundancy Arrays

We now introduce interstitial redundancy arrays with a range of redundancy ratios and analytically evaluate the reliability of these interstitial redundancy arrays.

A. Reliability Analysis of a (1, 4) Interstitial Redundancy Array

Figures 9A, 9B:
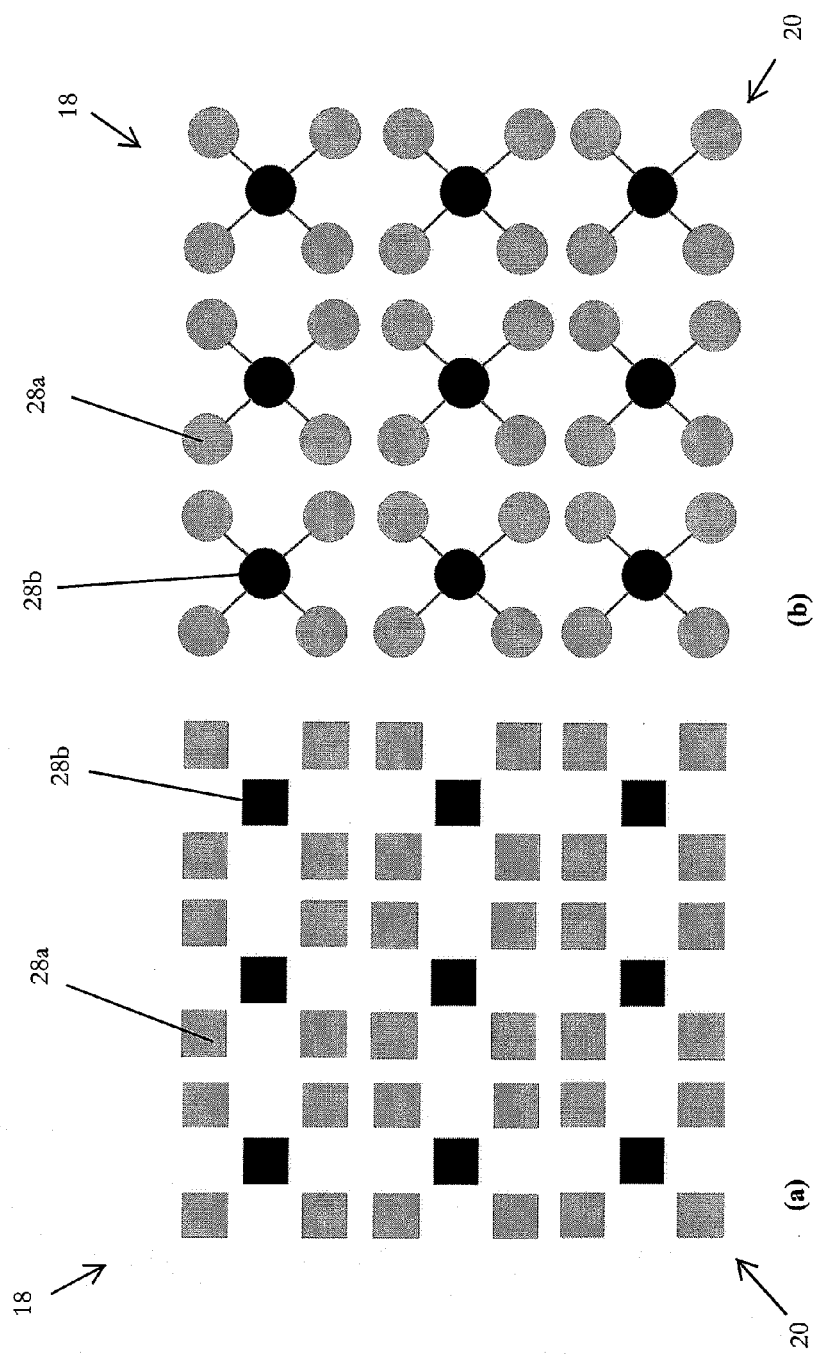
FIG. 9(a) is an example of (1, 4) interstitial redundancy array with spare module (black) at the interstitial sites of the primary modules (gray), and FIG. 9(b) the corresponding graph model.

In a (1, 4) interstitial redundancy array (FIG. 9(a)) each primary sensor module 28a can be replaced by a single spare sensor module 28b, while each spare sensor module 28b can replace one of four primary sensor modules 28a. The redundancy ratio for a (1, 4) interstitial redundancy array is 0.25.

In our analysis, unless indicated otherwise, we assume that the primary and the spare sensor modules 28b have equal failure rates since both have the same structure and function. As indicated above, the failure rate for each sensor module is considered to be a constant value, λ, with the reliability, $R_m$, specified by equation (1).

Let the grid of primary sensor modules 28a be of size m×n where m and n are even numbers. There are, then, mn clusters each with four primary sensor modules 28a and one spare sensor module 28b. The reliability of each cluster is given by (6):

$$R_{cluster(1,4)}(t) = \sum_{i=0}^{1} \binom{5}{i} R_m^{5-i}(t) C (1 - R_m(t))^i \tag{6}$$

The reliability of a (1, 4) interstitial redundancy array multielectrode array 18 of size m×n is given by (7):

$$R_{(1,4)}(t) = \left( \sum_{i=0}^{1} \binom{5}{i} R_m^{5-i}(t) C(1 - R_m(t))^i \right)^{\frac{mn}{4}} \quad (7)$$

$$= (R_m^5(t) + 5 R_m^4(t)(1 - R(t)))^{\frac{mn}{4}}$$

Where, the fault coverage factor, C, is assumed to be 1.

Figure 10:
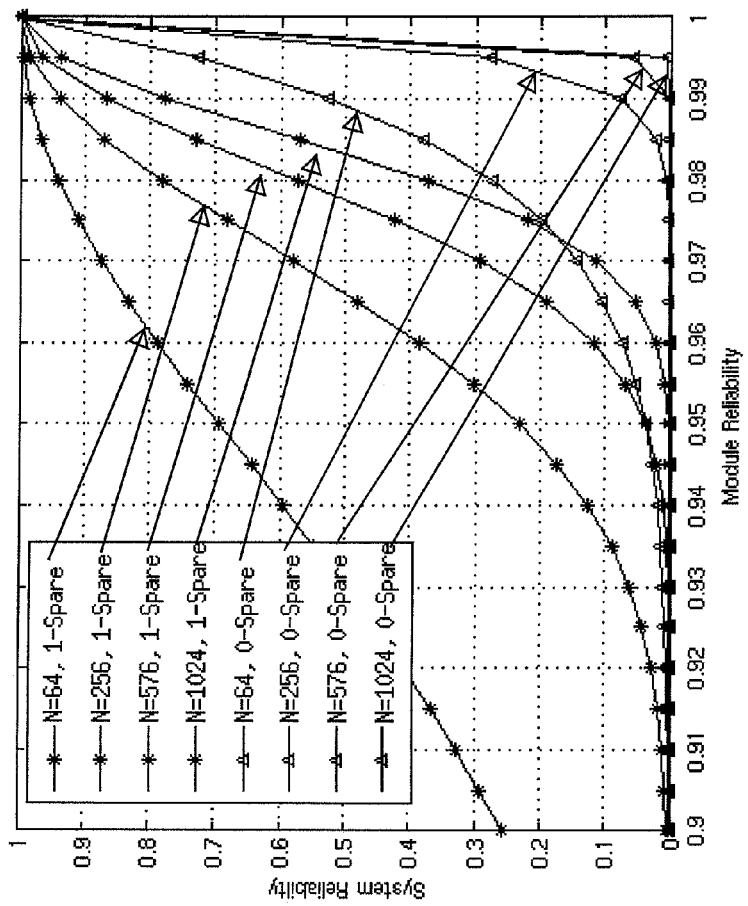
FIG. 10 shows the reliability of (1, 4) interstitial redundancy array multielectrode array with redundancy ratio of 0.25, C=1, and N=mn=64, 256, 576 and 1024. The (1, 4) interstitial redundancy array multielectrode arrays are compared to the corresponding multielectrode arrays without redundancy. It is evident that there is an increase in multielectrode array reliability with the interstitial redundancy array solution.

FIG. 10 shows the reliability of a (1, 4) interstitial redundancy array for different values of $R_m(t)$ and N, where N=mn and compares it to the reliability of the corresponding multielectrode arrays 18 without redundancy. It can be seen that interstitial redundancy improves multielectrode array 18 reliability.

B. Reliability Analysis of a (1, 6) Interstitial Redundancy Array

Figures 11A, 11B:
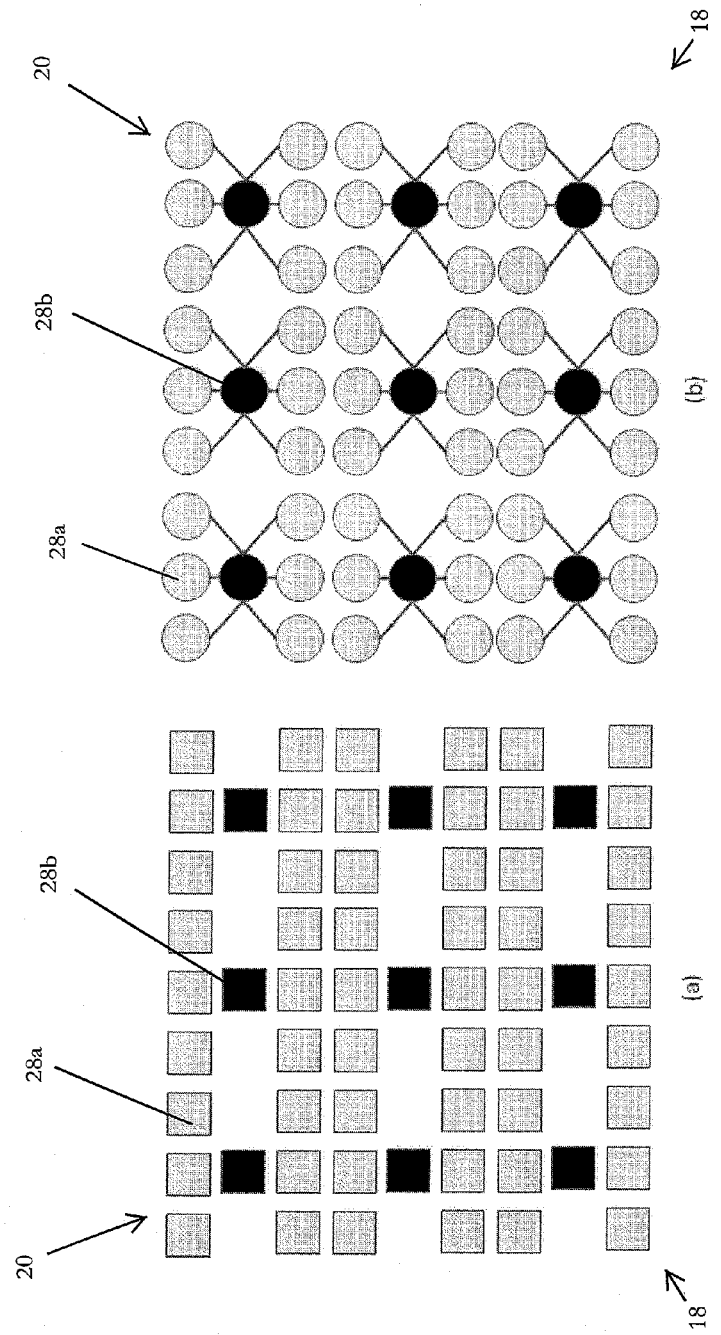
FIG. 11(a) shows a (1, 6) interstitial redundancy array grid design.
FIG. 11(b) shows the corresponding graph model. The gray nodes represent primary modules and the black nodes denote spare modules.

A (1, 6) interstitial redundancy array is shown in FIG. 11(*a*) and its corresponding graph model is shown in FIG. 11(*b*). Here, the redundancy ratio is 1=0.1667.

Like the (1, 4) interstitial redundancy array a (1, 6) interstitial redundancy array can be viewed as N/6 identical clusters where N, an integral multiple of 6, is the number of primary sensor modules 28*a* in the multielectrode array 18. Each cluster is composed of 6 primary sensor modules 28*a* and one spare sensor module 28*b*. The reliability of each cluster is the likelihood of having at most one failed sensor module among the seven sensor modules in the cluster and is given by (8).

$$R_{cluster(1,6)}(t) = \sum_{i=0}^{1} \binom{7}{i} R_m^{7-i}(t) C(1 - R_m(t))^i \quad (8)$$

The reliability of the (1, 6) interstitial redundancy array scheme with N primary sensor modules 28*a* is given by (9):

$$R_{(1,6)}(t) = \left( \sum_{i=0}^{1} \binom{7}{i} R_m^{7-i}(t) C(1 - R_m(t))^i \right)^{\frac{N}{6}} \quad (9)$$

$$= (R_m^7(t) + 7 R_m^6(t)(1 - R_m(t)))^{\frac{N}{6}}$$

Where, the fault coverage factor, C, is assumed to be 1.

Figure 12:
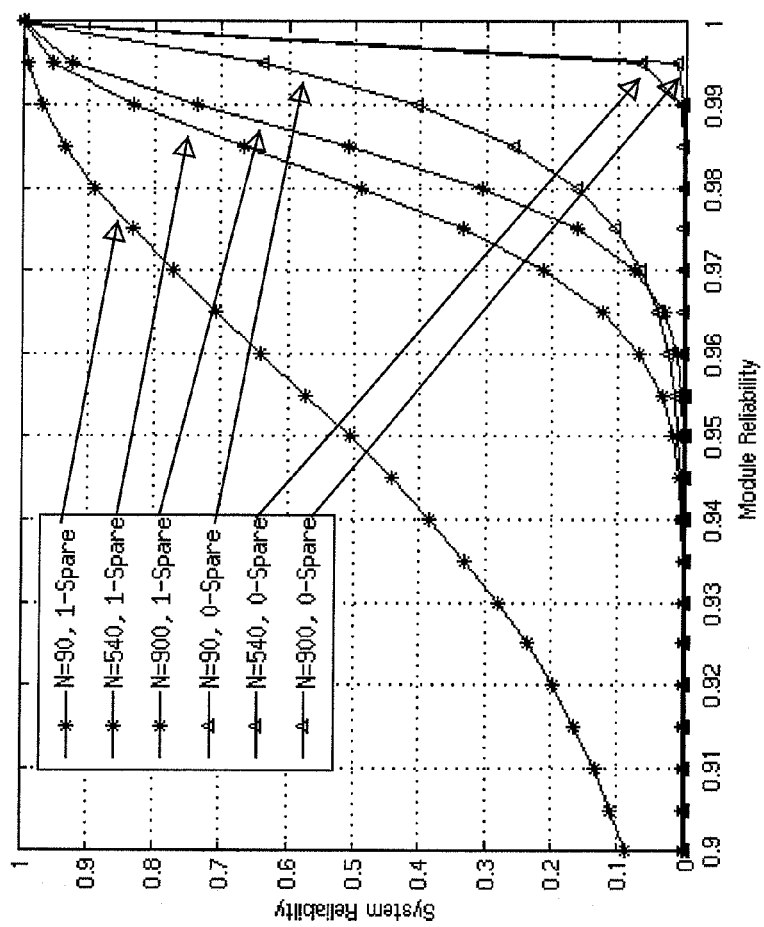
FIG. 12 shows the reliability of (1, 6) interstitial redundancy array multielectrode array with redundancy ratio of 0.25, C=1, and N=mn=90, 540 and 900 compared to the corresponding multielectrode arrays without redundancy.

FIG. 12 shows the reliability of a (1, 6) interstitial redundancy array for different values of $R_m(t)$ and N, and compares it to the reliability of the corresponding multielectrode array 18 without redundancy. The above analytical results confirm that interstitial redundancy improves multielectrode array 18 reliability.

C. Reliability Analysis of a (4, 4) Interstitial Redundancy Array

For fault-tolerant designs with higher redundancy ratio, such as the (4, 4) and (2, 6) interstitial redundancy arrays, analytical modeling to determine the reliability of a system is not straightforward due to the complex assignment of spare sensor modules 28*b*. However, the basic cluster based technique used above for the (1, 4) and (1, 6) interstitial redundancy arrays can still be used to derive approximate expressions for multielectrode array 18 reliability.

Consider the reliability analysis of the (4, 4) interstitial redundancy array shown in FIG. 5 whose redundancy ratio is 1. For a m×n (4, 4) interstitial redundancy array, the number of primary sensor modules 28*a*, p is mn and the number of spare sensor modules 28*b*, s is (m−1)(n−1). The reliability, $R_{(4, 4)}(t)$, of a (4,4) interstitial redundancy array with the coverage factor C can be approximated by viewing it as a p-out-of-(p+s) system, that is, an mn-out-of-(mn+(m−1)(n−1)) system, as given by (10):

$$R_{(4,4)}(t) = \sum_{i=0}^{s} \binom{s+p}{i} R_m^{s+p-i}(t) C(1 - R_m(t))^i \quad (10)$$

A second approximation introduced is that while four spare sensor modules 28*b* are available to replace each non-boundary primary sensor module 28*a*, each of the four corner primary sensor modules 28*a* can be replaced by only one spare sensor module 28*b* and each of the remaining primary sensor modules 28*a* on the boundary can be replaced with two spare sensor modules 28*b*. The corner sensor modules can be considered as a 1-out-of-2 system. Thus, the reliability of the sub-system of four corner primary sensor modules 28*a* can be given by (11):

$$R_{corner(4,4)}(t) = \left( \sum_{i=0}^{1} \binom{2}{i} R_m^{2-i}(t) C(1 - R_m(t))^i \right)^4 \quad (11)$$

Among the remaining boundary primary sensor modules 28*a* and their corresponding spare sensor modules 28*b*, there is one set of 2(m−2) primary sensor modules 28*a* with 2(m−3) spare sensor modules 28*b* and one set of 2(n−2) primary sensor modules 28*a* with 2(n−3) spare sensor modules 28*b*. The reliability of the sub-system composed of these sensor modules can be approximated by 2(m−2) out-of-(4m−10) and 2(n−2) out-of-(4n−10) systems. Thus, the reliability of such a subsystem is given by (12), (13), (14):

$$R_{boundary(4,4)}(t) = R_{boundary1(4,4)}(t) R_{boundary2(4,4)}(t) \quad (12)$$

where, $$R_{boundary1(4,4)}(t) = \sum_{i=0}^{2(m-3)} \binom{4m-10}{i} R_m^{4m-10-i}(t) C(1 - R_m(t))^i \quad (13)$$

and, $$R_{boundary2(4,4)}(t) = \sum_{i=0}^{2(n-3)} \binom{4n-10}{i} R_m^{4n-10-i}(t) C(1 - R_m(t))^i \quad (14)$$

Finally, the reliability of the sub-system composed of the remaining set of (m−2)(n−2) primary sensor modules 28*a* with (m−3)(n−3) spare sensor modules 28*b* can be approximated as a (m−3)(n−3) out-of-(2 nm−5m−5n+13) system, given by (15):

$$R_{other(4,4)}(t) = \quad (15)$$

$$\sum_{i=0}^{(m-3)(n-3)} \binom{2mn - 5m - 5n + 13}{i} R_m^{4m-10-i}(t) C(1 - R_m(t))^i$$

Thus, the reliability of a (4, 4) multielectrode array 18 can be obtained by combining all the sub-system reliabilities, as shown in (16):

$$R_{(4,4)}(t) = R_{corner(4,4)} R_{boundary1(4,4)} R_{boundary2(4,4)} R_{other(4,4)} \quad (16)$$

Figure 13:
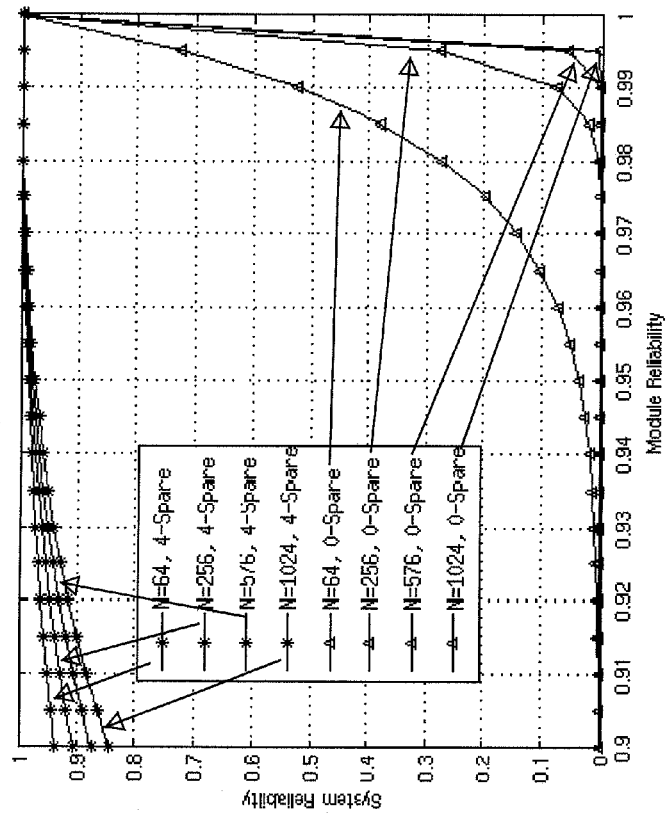
FIG. 13 shows the reliability of (4, 4) interstitial redundancy array multielectrode array with redundancy ratio of 1, C=1, and N=mn=64, 256, 576 and 1024 compared to the corresponding multielectrode arrays without redundancy.

FIG. 13 shows the reliability of a (4, 4) interstitial redundancy array for different values of $R_m(t)$ and N and compares it to the reliability of the corresponding multielectrode array 18 without redundancy.

Figure 14:
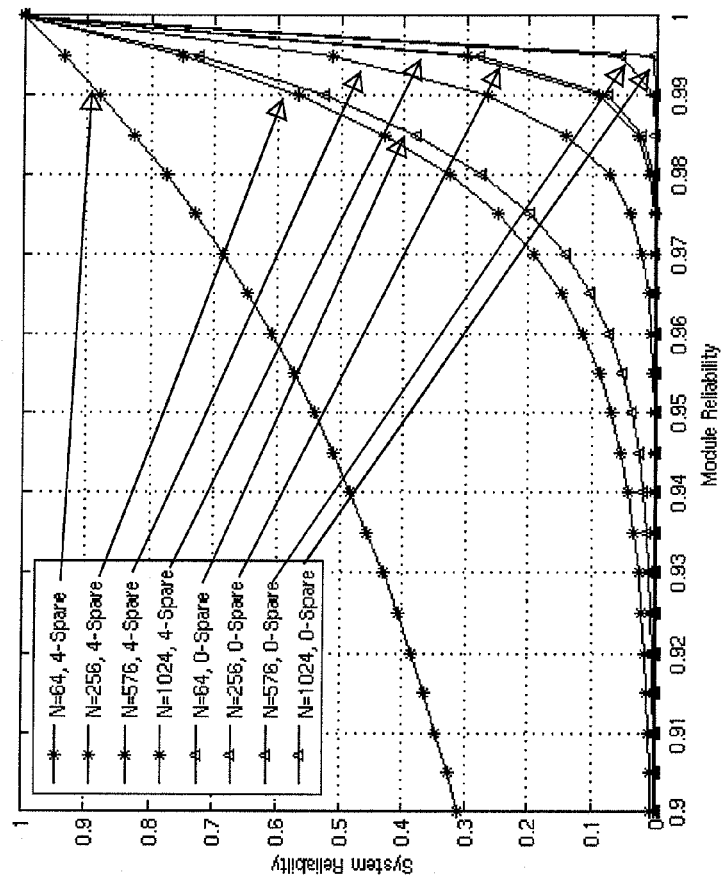
FIG. 14 shows the reliability of a (4, 4) interstitial redundancy array multielectrode array with redundancy ratio of 1, and fault coverage factor, C=0.95, and N=mn=64, 256, 576 and 1024, and the reliability of the corresponding multielectrode arrays without redundancy.
Figure 15:
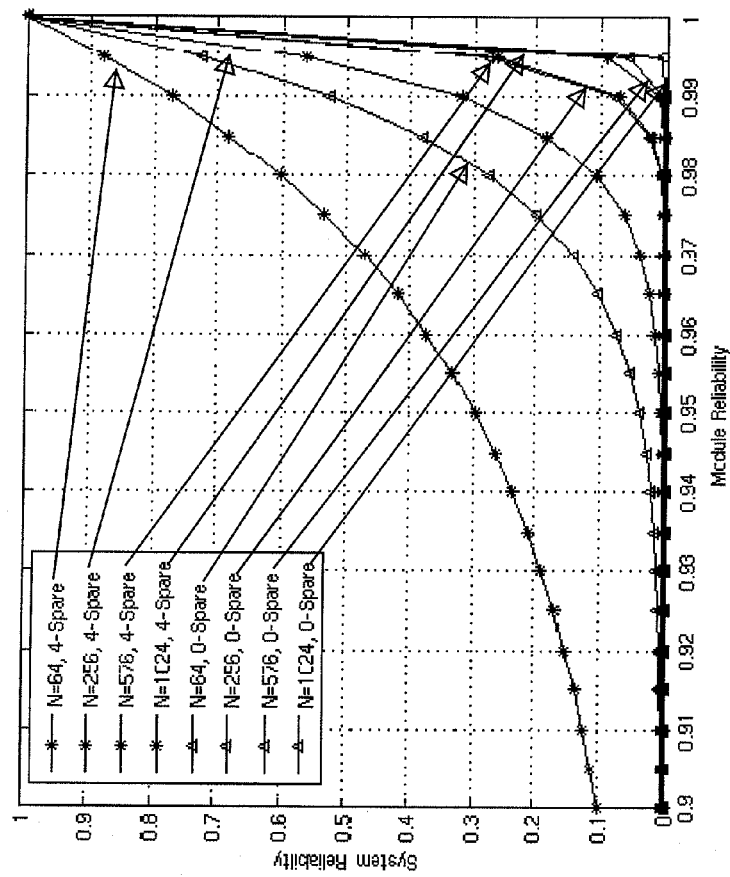
FIG. 15 shows the reliability of a (4, 4) interstitial redundancy array multielectrode array with redundancy ratio=1, and fault coverage factor, C=0.90, and N=mn=64, 256, 576 and 1024, and the reliability of the corresponding multielectrode arrays without redundancy.

FIGS. 14 and 15, show the system reliability of (4, 4) interstitial redundancy array multielectrode arrays 18, with coverage factor C<1, C=0.95 and C=0.90, respectively.

D. Reliability Analysis of a (2, 6) Interstitial Redundancy Array

Figure 16:
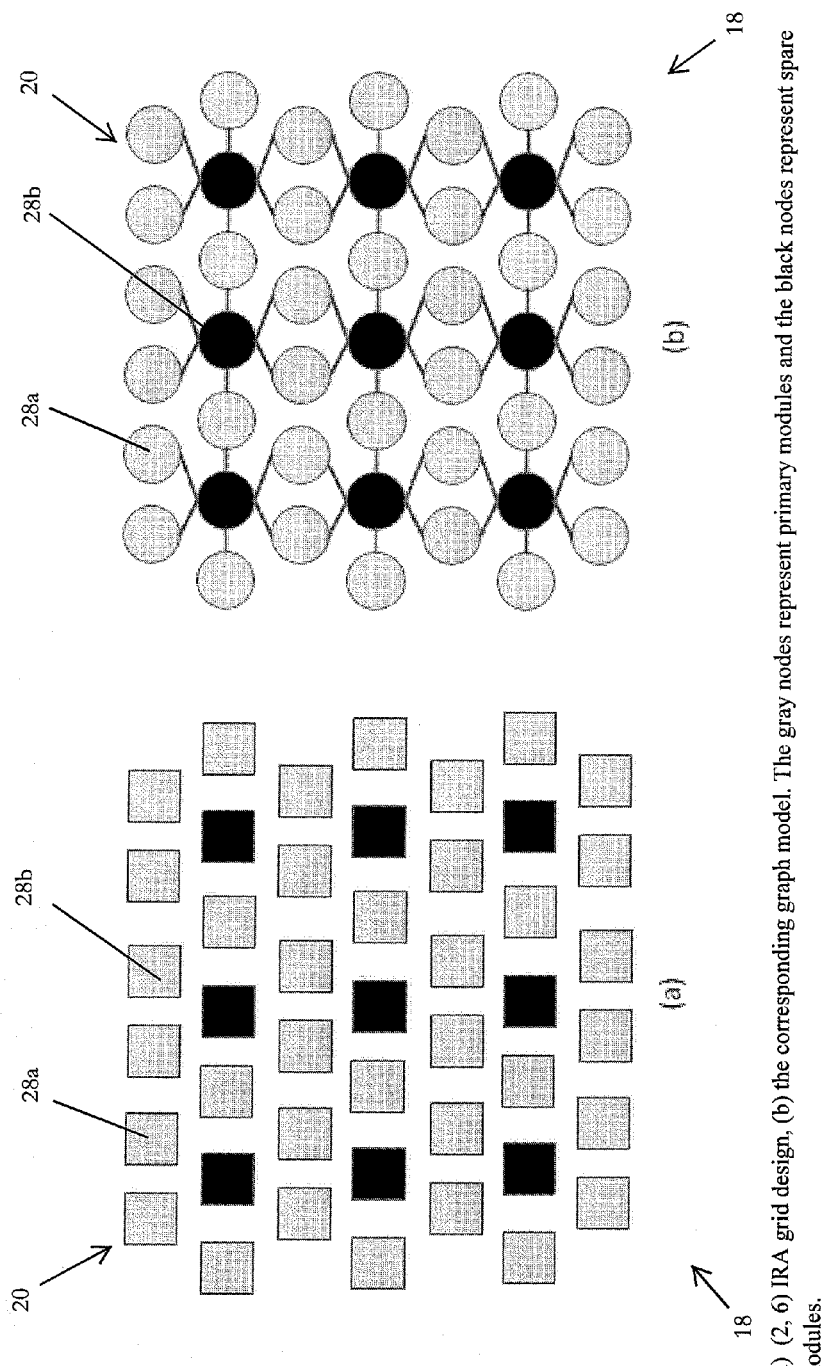
FIG. 16(a) shows a (2, 6) interstitial redundancy array grid design.
FIG. 16(b) shows the corresponding graph model. The gray nodes represent primary modules and the black nodes represent spare modules.

Next, consider the (2, 6) interstitial redundancy array configuration displayed in FIG. 16(a). This configuration can be considered to be composed of identical clusters, each with 11 primary and two redundant sensor modules as shown in FIG. 16(a). Thus the cluster method used above can be applied to estimate the reliability of this interstitial redundancy array. As shown in FIG. 14(a), the multielectrode array 18 can be partitioned in such a way that each partition is composed of two spare sensor modules 28b and all the primary sensor modules 28a adjacent to these two spare sensor modules 28b. Since all 10 boundary sensor modules of a partition are shared by adjacent partitions, only half of them need to be considered for this analysis. Thus an equivalent cluster is composed of six, (that is, 10/2+1) primary sensor modules 28a and 2 spare sensor modules 28b, that is, each primary sensor module can be replaced by one of the two spare sensor modules 28b, and each spare sensor module 28b can be used to replace one of the six primary sensor modules 28a.

The reliability of each cluster is the likelihood of having at most two faulty sensor modules among the 8 sensor modules, given by (17), $$R_{cluster(2,6)}(t) = \sum_{i=0}^{2} \binom{8}{i} R_m^{8-i}(t) C(1 - R_m(t))^i \quad (17)$$

Assuming that the (2, 6) interstitial redundancy array with N primary sensor modules 28a can be approximately divided into N/6 clusters, and the failures are independent, the reliability of the (2, 6) interstitial redundancy array can be calculated by (18):

$$R_{cluster(2,6)}(t) = \left( \begin{array}{c} R_m^8(t) + 8R_m^7(t)(1 - R_m(t)) + \\ 28R_m^6(t)(1 - R_m(t))^2 \end{array} \right)^{N/6} \quad (18)$$

Where, the fault coverage factor, C, is assumed to be 1.

Figure 17:
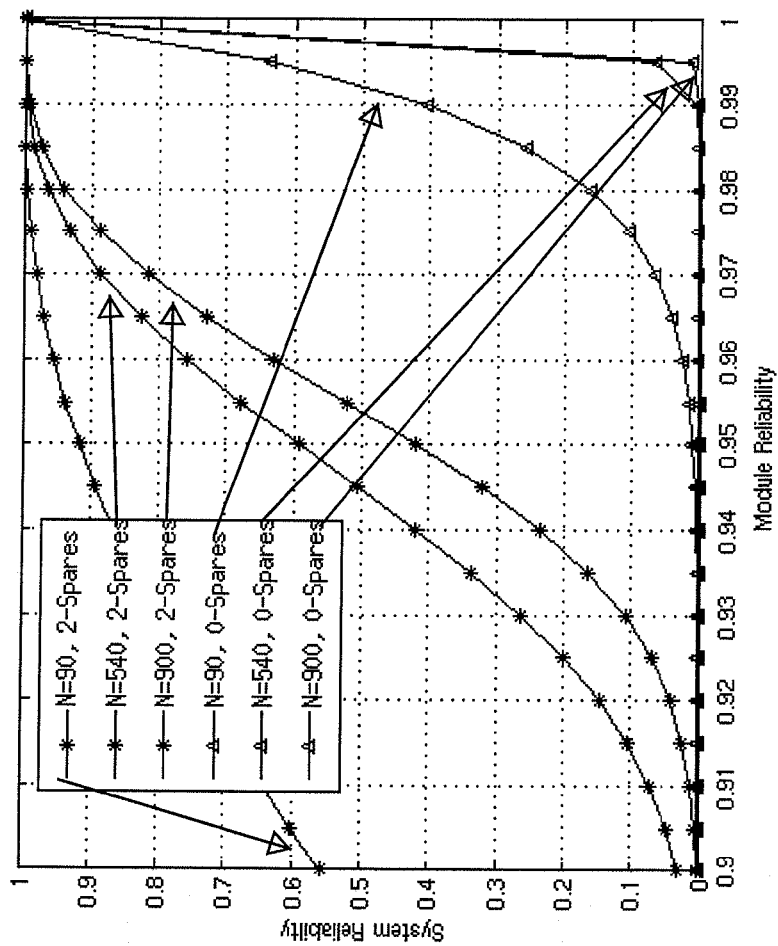
FIG. 17 shows the reliability of (2, 6) interstitial redundancy array multielectrode array with redundancy ratio of 0.33, C=1, and N=mn=90, 540 and 900, and the reliability of the corresponding multielectrode arrays without redundancy.

FIG. 17 shows the reliability of (2, 6) interstitial redundancy array for different values of $R_m(t)$ and N compared with the reliability of the corresponding multielectrode arrays without redundancy.

E. Comparison of Reliability of (1, 4), (1, 6), (2, 6), and (4, 4) Interstitial Redundancy Array Designs FIG. 18 shows the effect of sensor module reliability on the system reliability of (4, 4), (2, 6), (1, 4) and (1, 6) interstitial redundancy array fault-tolerant design for different numbers of primary sensor modules 28a and with fault coverage, C=1.

Figure 18:
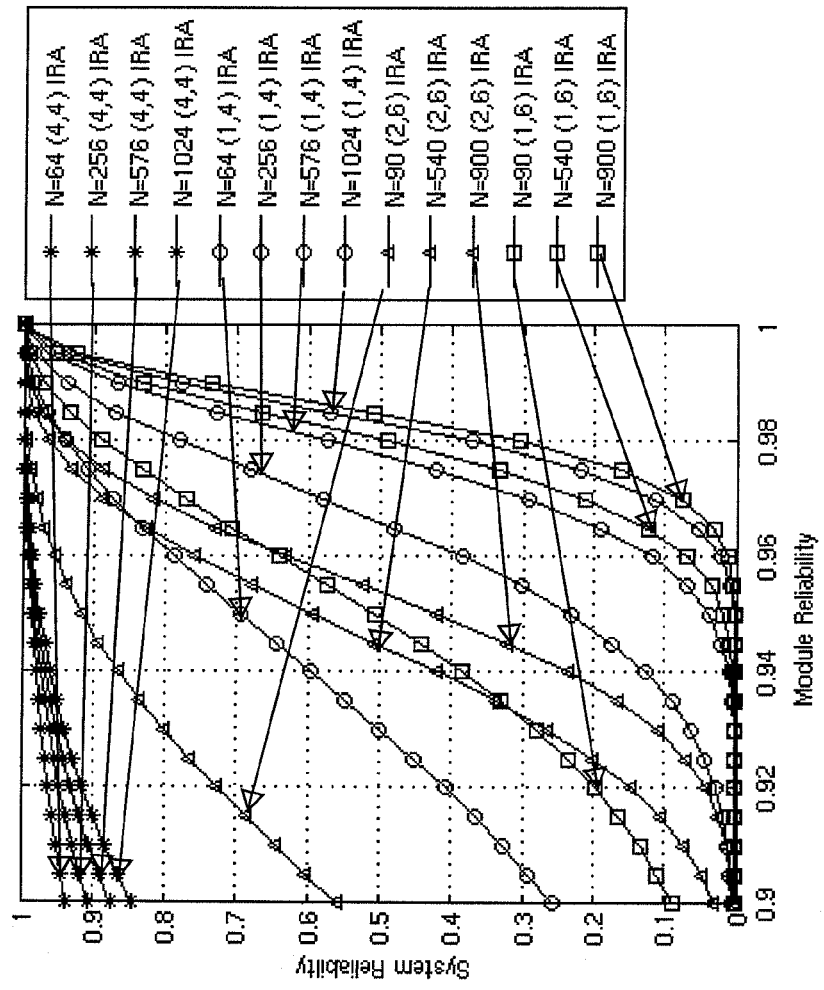
FIG. 18 shows the reliability of (1, 6), (1, 4), (2, 6), and (4, 4) interstitial redundancy arrays with C=1 for different sizes and module reliability.

From FIG. 18 it can be concluded that the system with a higher level of redundancy, such as the (4, 4) interstitial redundancy array, should be used when sensor module reliability is low while systems with lower redundancy can be used when sensor module reliability is high.

The interstitial redundancy arrays considered here had redundancy ratios which ranged from 0.16 to 1.0. We note that a redundancy ratio higher than one is possible (such a multielectrode array 18 would have more spare sensor modules 28b than primary sensor modules 28a), and the design and analysis developed here can be readily extended to such interstitial redundancy arrays. Further, we consider a multielectrode array 18 as fault-free after reconfiguration, if and only if all the faulty primary sensor modules 28a can be replaced by a fault-free spare sensor module 28b. Higher system reliability can be achieved, if a smaller number of working sensor modules 28a suffices to perform the required function. That is, higher reliability is possible if a smaller number of working sensor modules suffices to achieve the desired function, that is, a graceful degradation of multielectrode array function is acceptable.

Figure 19:
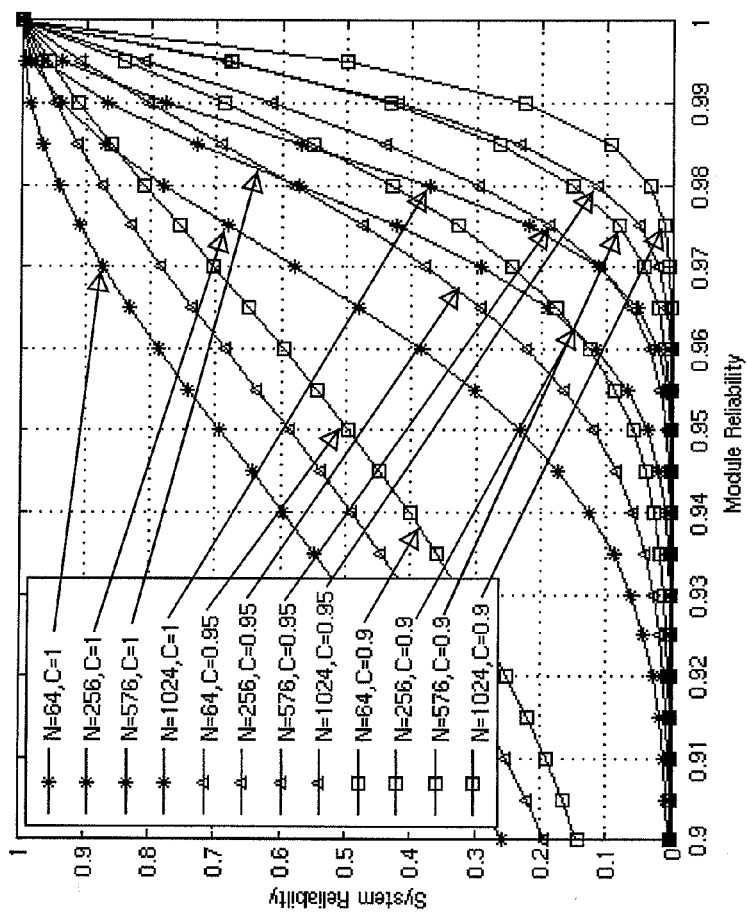
FIG. 19 shows the reliability of a (1, 4) interstitial redundancy array with C=1, 0.9 and 0.95 for multielectrode arrays of different sizes and varying module reliability.
Figure 20:
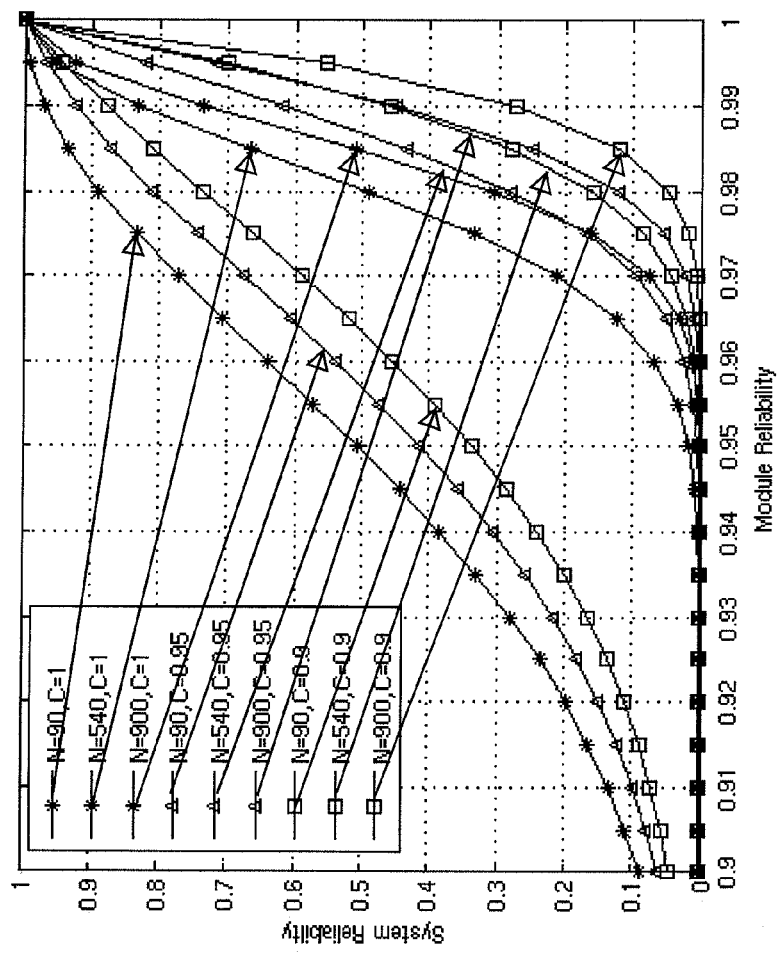
FIG. 20 shows the reliability of a (1, 6) interstitial redundancy array with C=1, 0.9 and 0.95 for multielectrode arrays of different sizes and varying module reliability.
Figure 21:
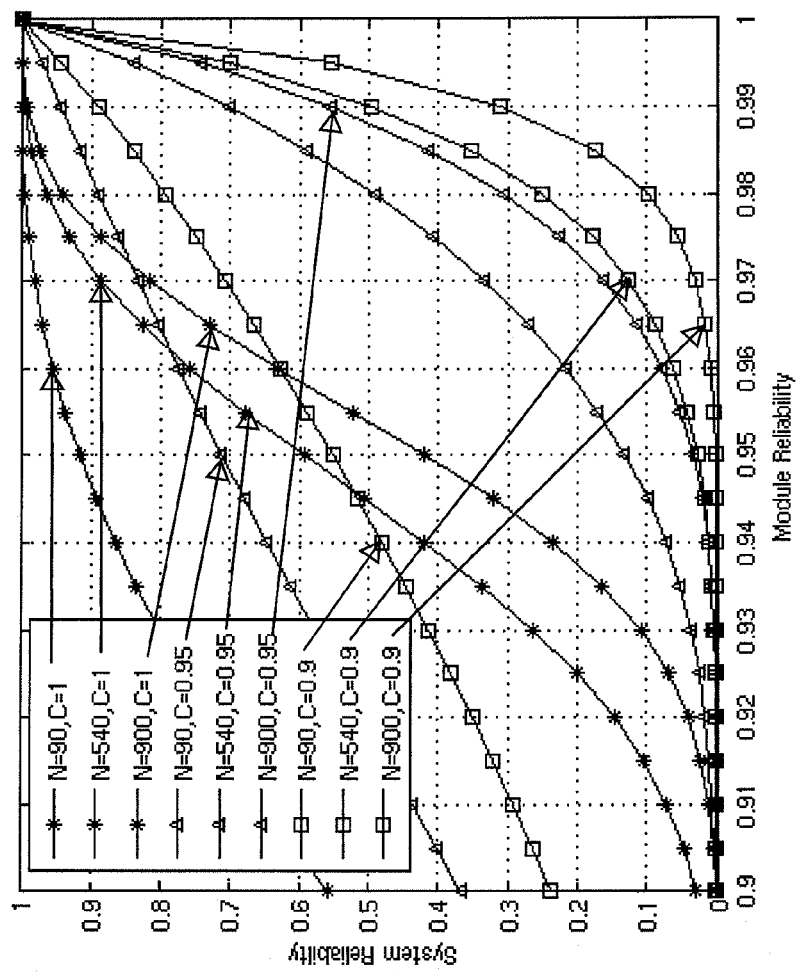
FIG. 21 shows the reliability of a (2, 6) interstitial redundancy array with C=1, 0.9 and 0.95 for multielectrode arrays of different sizes and varying module reliability.
Figure 22:
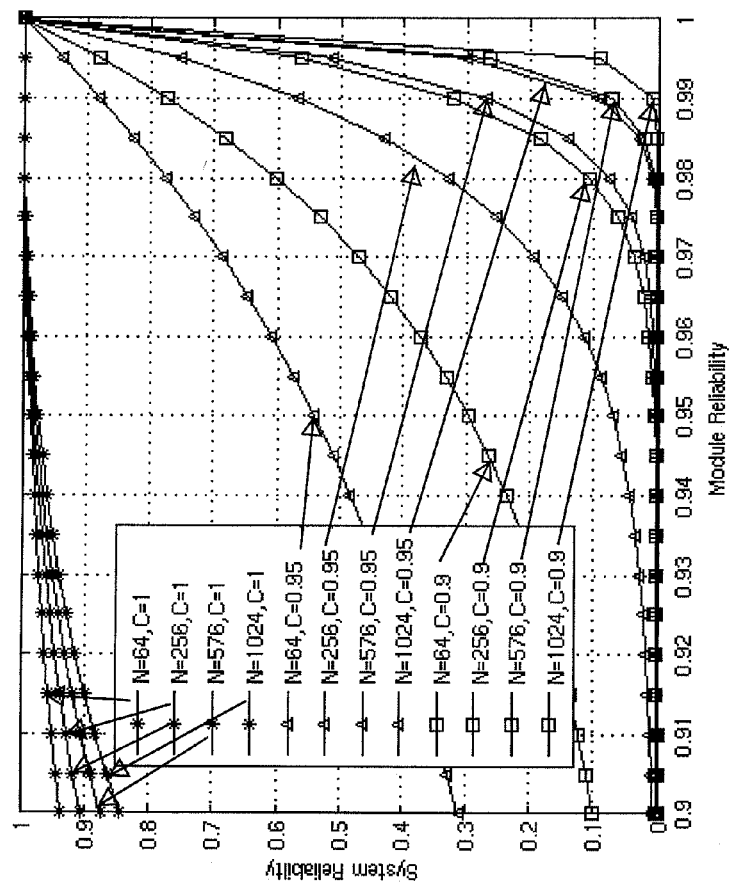
FIG. 22 shows the reliability of a (4, 4) interstitial redundancy array with C=1, 0.9 and 0.95 for multielectrode arrays of different sizes and varying module reliability.

Further analysis suggests that, given a situation where the fault coverage factor 'C' is less than 1, the redundant system continues to perform better than a system without redundancy. FIG. 19, displays the reliability analysis of a (1, 4) interstitial redundancy array for C=1, 0.95 and 0.90. Similarly, FIGS. 20, 21 and 22 display reliability analysis when C<1 for (1, 6), (2, 6) and (4, 4) interstitial redundancy array systems respectively. It can be noted that a system with higher fault coverage factor should be used with lower sensor module reliability and a system with lower coverage factor should be used when the sensor module reliability is high.

V. Simulation Results

Figure 23:
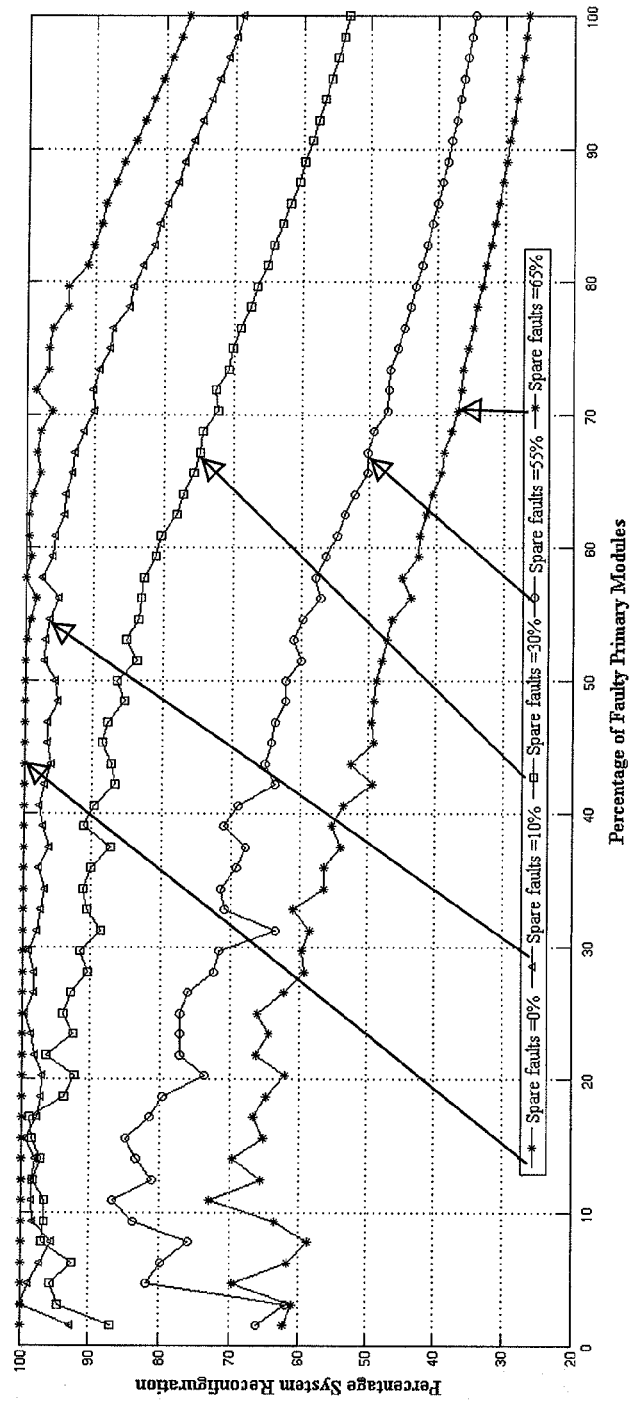
FIG. 23 shows simulation of fault reconfiguration for a (4, 4) interstitial redundancy array with grid size N=64 and with a fault-coverage factor, C=1. There is a steady decrease in percentage system reconfiguration with increasing percentage of primary faults.
Figure 24:
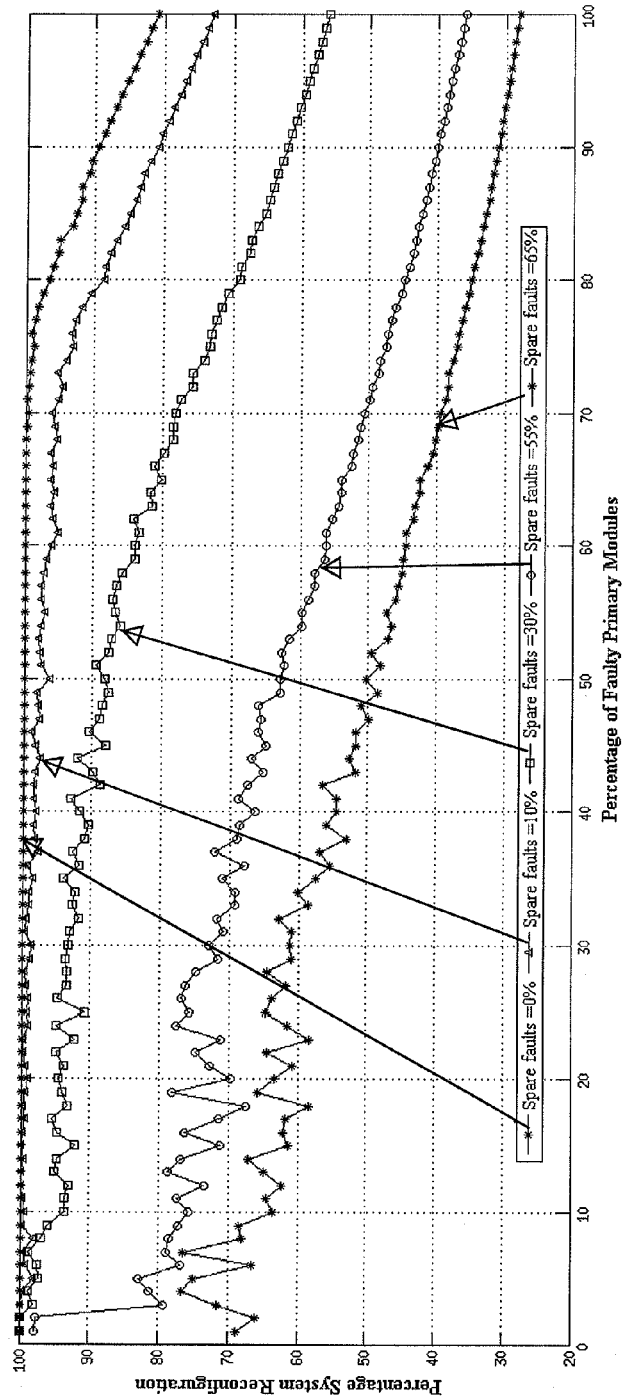
FIG. 24 shows simulation of fault reconfiguration for a (4, 4) interstitial redundancy array with grid size N=100 and with a fault-coverage factor, C=1.

We now present an extended simulation of the interstitial redundancy array solution. In this simulation we create random faults of both primary and spare modules and attempt to reconfigure the multielectrode array. We perform 15 simulations for each data point displayed. We display the percentage of instances that a successful reconfiguration of the electrode array was possible. By a successful reconfiguration we mean that a functioning spare module could be assigned to every failed primary module. Though this analysis is performed for the (4, 4) interstitial redundancy array, the results can be readily extended to other interstitial redundancy arrays. FIGS. 23 and 24 display the effect of faults in primary and spare sensor modules 28b of a (4, 4) interstitial redundancy array, with grid sizes N=64 and 100. The percent system reconfiguration obtained is plotted as a function of percentage of faulty primary sensor modules 28a with the percentage of faulty spare sensor modules 28b varying from 0-65%. Faults were injected in a random pattern within the multielectrode array 18, and the simulation was run to compute the percentage of fault reconfiguration using the maximum-matching algorithm, as described herein.

From FIGS. 23 and 24 it can be noted that the percent fault reconfiguration has a higher variance when the percentage of primary faults are low and percentage of spare faults are high as compared to the case when the percentage of primary faults are high and the percentage of spare faults are low. This is because in the presence of spare faults the percentage system reconfiguration varies depending on the spatial relationship between primary and spare faults. If most of the faulty primary sensor modules 28a are surrounded by faulty spare sensor modules 28b, the system reconfiguration encounters a 'worst-case' scenario. In contrast if most of the faulty primary sensor modules 28a are surrounded by healthy spare sensor modules 28b the system reconfiguration encounters a 'best-case' scenario. Due to these two extreme cases, the variance in the average system reconfiguration is much higher when the percentage of spare faults is considerably greater than the percentage of primary faults. We can also observe that the system reconfiguration is nearly 90% when faulty spare sensor modules 28b are between 0-30% and faulty primary sensor modules 28a are between 0 and 50%. With increasing percentage of faulty spare sensor modules 28b there is a decrease in system reconfiguration as expected. When the number of faulty primary sensor modules are greater than 50%, we observe, in FIGS. 23 and 24, a decrease in the variance of the average system reconfiguration. This is because as increasing numbers of primary sensor modules 28a become faulty there is a decrease in the difference between the best-case and the worst-case scenarios. Eventually, the variance in system reconfiguration minimizes. However, it is important to note that the proposed system offers better reliability (percent system reconfiguration≈30%) even with a high percentage of faulty spare sensor modules 28b (≈65%) and very high faulty primary sensor modules 28a (≈90%), as compared to a system without redundancy.

Note that all the discussed multielectrode array 18 architectures had spare sensor modules 28b which were not on the boundary, (i.e. redundancy ratio 1). The performance of the proposed multielectrode array 18 architectures can be further improved by incorporating spare sensor modules 28b on the boundary.

VI. Discussion of the Present Fault-Tolerant Design

The two fault-tolerant solutions in accordance with the present invention increase the dependability of a multielectrode array 18. The two fault-tolerant solutions of the present invention involve redundant sensor modules that act as spare sensor modules 28b and replace the primary sensor modules 28a, should they fail. This approach increases the probability of dependable monitoring of the electrical activity of the brain.

Redundancy in accordance with the present invention increases cost and development time and may impact power consumption, heat generation, mass, and volume. Higher redundancy increases component area and renders these issues more critical requiring the use of appropriate conservation strategies. A fault-tolerant design thus requires a trade-off between dependability and the amount of redundancy required to achieve it. The fault-tolerant methods are assumed to be designed with cold spare circuitry, where a spare sensor module 28b is switched on only if it is brought online during reconfiguration. Cold spare reconfiguration helps conserve power, extends life of the spare sensor module 28b, and facilitates thermal management of an implantable device. We have considered a sensor module to be composed of a sensor 12a, 12b and its associated amplifier 30a, 30b. The sensor 12a, 12b and the amplifier 30a, 30b can be considered separately and a fault-tolerance strategy can be evolved which treats the sensor and the amplifier as separate components with different redundancy ratios for each, and allows separate re-configuration to be performed for sensors, their amplifiers and the remainder of the electronics.

It is appreciated two methods to improve the reliability of multielectrode arrays 18 are disclosed in accordance with a preferred embodiment of the present invention. The first solution utilizes rows or columns of spare sensor modules 28b to replace faulty primary sensor modules 28a. In this approach the reconfiguration strategy is simple but the hardware overhead is substantial. The second solution uses space redundancy with local configuration capability where spare sensor modules 28b are placed in the interstitial sites of the multielectrode array 18 and can replace faulty neighboring primary sensor modules 28a. The reconfiguration process in interstitial redundancy is relatively simpler since it involves only neighboring fault-free spare sensor modules 28b. The results indicate a considerable improvement in system reliability with redundancy.

It is appreciated the two fault-tolerant solutions of the present invention have different degrees of complexity and overhead. The reconfiguration strategy for the row or column based solution is simple. It does not require, for example, a graph based matching to obtain a result. The reconfiguration for the spare row or column solution may require, however, replacement of fault-free modules. The reconfiguration for the interstitial redundancy array is more complex, however, it does not involve replacement of fault-free modules. The two solutions can be used separately or together. The difference in complexity and overhead of the two solutions can be used to advantage. For example, the first solution can be used by an embedded chip to arrive at a reconfiguration. The second solution can then be tried at another point in time, for example during a visit to a physician's office or by the external device, and replace the result obtained by the first solution.

A. Impact of Assumptions Made in the Analysis

It should be appreciated that we have made two assumptions in the analysis presented. First, we have assumed that the failure rate is constant. Second, we have assumed that the failures are independent. If these assumptions do not hold this will not impact the correctness of the solutions described, it will however impact the accuracy of the analysis which has been presented. If these assumptions do not hold the analysis which has been presented will be approximately but not exactly correct.

B. Non-Two-Dimensional Form-Factors

The fault-tolerant embodiments described above were developed for a two dimensional multielectrode array 18. We note, these solutions can be readily be extended to other form-factors. For example, the concepts described here can be extended to a linear multielectrode array 18 of distributed sensors with spare sensors integrated with primary sensors on the linear array. The concepts described here can also be extended to the inner or outer surface of a tube. To do this we consider a fault tolerant sensor array to be placed on a 2D rectangular surface as described here. This rectangular surface can then be considered to be rolled so that two opposite edges of the 2D rectangular surface touch each other. A surface rolled in this manner will form a tube. The sensing array will be placed on the inner and/or outer wall of this tube depending on which surface of the 2D surface the sensors were placed on. The concepts developed here can also be extended to the surface of other 3D structures such as a sphere with primary and spare sensors placed at different latitudinal or longitudinal points on the surface of the sphere. The reconfiguration algorithm described here can readily be extended to these non-2D form factors so that there is continuity across the entire surface of sensors. The solutions described here are also not limited to electrophysiological sensors or the brain. The solutions can be readily extended to any organ which has to be reliably sensed by an implanted array of sensors. Other sensors, which may be considered, include glucose sensors, or biosensors to measure neurochemistry.

C. Detection and Isolation of Faults

Before a faulty sensor module can be addressed in the manner discussed above, it must be identified. The detection can be performed through analysis using signal processing and/or statistical criteria of sensor signal quality. The detection and isolation of sensor module faults can also be performed by utilizing constraints that are imposed by the system that is being measured along with the sensor configuration. These constraints, which are sometimes termed redundancy, can be imposed directly in hardware (hardware redundancy using multiple identical sensors or systems measuring the same parameter) or indirectly by the implantable device itself (analytic redundancy using known analytical relationships between system variables). When sensor readings no longer satisfy the redundancy relations, a fault is detected. Fault isolation occurs by determining if subsets of remaining sensors and constraints are still satisfied. In accordance with a preferred embodiment of the present invention, such fault detection is carried out by the internal chip control system 36 of the multielectrode array.

While it is appreciated fault detection may be achieved in various manners, in one possible embodiment of the present invention the analytic redundancy relations is expressed using a parity space. To introduce the parity space methods, consider the example of hardware redundancy, where several sensor modules are used to measure an identical physical parameter. In this case, the sensors must all give the same reading (within a given tolerance), otherwise a fault is declared. If we collect the n sensor measurements into a vector $x=[y_1\ y_2\ \ldots\ y_{en}]^T$, we require the vector x to stay on (or close to) the one dimensional vector subspace defined by the basis function $e=[1\ 1\ \ldots\ 1]^T$, otherwise a fault is declared. The vector e then defines the sensor subspace. Using projection operators, a sensor measurement vector can be projected onto the sensor subspace (the allowable subspace) and the complement of this subspace, so that $x=x_s+x_c$, where is $x_s$ is the part of the measurement in the sensor subspace, while $x_c$ is in the complement. A parity check occurs by determining if $x_c$ is sufficiently small. Because of noise it is common to apply filtering before this determination is made. This notion can be extended to other situations where redundancy is either not as strong or not as direct by introducing more complex allowable subspaces.

Parity space methods may be applied to dynamic systems by including delayed values of sensor measurements (this is how parity space was first defined). Chow, E. Y. and Willsky, A. S., *Analytical Redundancy and the Design of Robust Failure Detection Systems*, IEEE Transactions on Automatic Control, 1984. 29, p. 603-614. For example, consider a two sensor network. Associated with each sensor is a sensor subspace that defines the expected measurement space. Each axis represents a sensor measurement taken at a given delay. For example, for sensor 1, we may test the vector $v=[y_1(k)\ y_1(k-1)\ y_2(k)]$, where $y_i(k)$ is the sensor measurement for sensor i at sample k. This could be useful, for example, in the case when $y_1$ is a thermocouple measurement and $y_2$ is a measure of the rate of heat flow. We would expect a proportional relationship between $y_1(k)-y_1(k-1)$ and $y_2(k)$, which should result in the identification of the sensor subspace basis function [1−1 a]. As the system dynamics become more complex, more sensors or delays can be added. In general, the more dimensions we include in the sensor subspace, the greater the power of the fault detection (as long as uncertainties are accounted for correctly). However, there are clearly diminishing returns if one includes a sensor measurement from the distant past, or includes a sensor measurement that is uncorrelated with the sensor of interest.

In the dynamic case, the combination of a parity check along with residual filtering results in a structure equivalent to what is usually called an estimator, and the celebrated Kalman filter, can be used. Everything described so far has used linear relationships between sensor measurements—implying that the system operates in a mainly linear manner. Sensor subspaces and parity relations can be extended to the nonlinear case if required.

The strategy as applied to the present brain implantable device has two distinct advantages. First, by including an embedded capability of acquiring, sharing, and analyzing data, the development of analytic relationships directly from data is possible, reducing the modeling burden. Linear sensor subspaces can be identified on-line from typical process data using Principal Component Analysis (PCA) Dunia, R. and Qin, S. J., *A Unified Geometric Approach to Process and Fault Identification and Reconstruction: The Unidimensional Fault Case*, Comp. Chem. Eng., 1998. 22: p. 927-943; Dunia, R. and Qin, S. J., *A Subspace Approach to Multidimensional Fault identification and Reconstruction*, AIChE Journal, 1998. 44: p. 1813-1831. This method finds the subspace of a given dimension that best fits a collection of data, and subsequently, new data measurements are monitored for how well they keep to this identified subspace. In a network implementation, the first task is to decide which measurements will be used to build the sensor subspace. Sensor topology may be used to derive possible sensors to include, or it may be guided by user input. Unnecessary measurements can be pruned depending on the required power of the fault detection test. Second, new developments for residual analysis such as set-based estimators can reduce the reliance on particular stochastic assumptions on noise and disturbances.

D. Fault Tolerant Computing

It is appreciated fault-tolerant computation may be achieved within the spirit of the present brain implantable device 10. The present brain implantable device incorporates the ability to recover from transient faults in the internal chip control system 36 of the multielectrode array 18.

It is appreciated such an internal chip control system 36 and/or central node may utilize a multi-core processor for the embedded application. One attractive option is time redundancy together with hardware redundancy. Faults in the processor are detected at the system level and the execution is replicated on unused cores. In another approach the task is replicated in two communicating threads in which one of the threads will trail the other thread. Such threads may be executed in the embedded and external units. The trailing thread will repeat the computations performed by the first thread and the results produced by these threads will be compared.

In a further embodiment, the present brain implantable device could use parallelism in the signal processing algorithms. The present brain implantable device could use analytical models for different parallelization schemes capturing multi-core specific architectural features. Analytical models for parallel programs can provide simple qualitative insights and bounds on program scalability. Adve, S. and Vernon, M., *Parallel Program Performance Using Deterministic Task Graph Analysis*, ACM Transactions on Computer Systems, 2004, 22(1): p. 94-136. First, time and space complexity of the underlying sequential algorithm will be determined. In parallelizing the algorithm, the data dependencies will be analyzed, candidate parallel patterns will be identified, Mattson, T., Sanders, B., and Massingill, B., *A Pattern Language for Parallel Programming*, Addison Wesley Software Patterns Series, 2004, and mapping and synchronization of the candidate patterns on to the underlying architecture will be performed to minimize inter-core computation and main memory access. Bounds for the total time taken, the memory bandwidth, the interconnect bandwidth and the number of floating point operations will be then estimated using results from the architecture characterization step. Appropriate simplifications may be made at this stage to make the problem analytically tractable while providing close form expressions that allow the programmer to readily identify performance trade-offs.

It is appreciated that the present invention specifically relates to sensing the electrophysiological activity of the brain with a brain implantable device. This could be applicable to epilepsy or locked-in syndrome. The concepts underlying the present invention more generally are applicable for sensing any organ or set of organs with an array of implanted sensors. The sensors could include electrophysiological sensors, but are not limited to electrophysiological sensors, they could include bio-sensors for neurotransmitters or glucose sensors in diabetes or any array of sensors from which we seek to record reliable measurements over an extended period of time of years).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A multielectrode array with fault-tolerance for use in conjunction with a brain implantable device, comprising:
 a sensor grid composed of a plurality of sensors, the plurality of sensors including primary sensors and spare sensors, wherein each of the primary sensors is linked to an amplifier to define a primary sensor module and each of the spare sensors is linked to an amplifier to define a spare sensor module, the spare sensors being placed in interstitial sites between primary sensors;
 signal processing circuitry associated with the plurality of sensors identifying faulty primary sensor modules and available spare sensor modules; and
 a control system associated with the sensor grid for replacing faulty primary sensor modules with spare sensor modules via reconfiguration of the plurality of sensors.

2. The multielectrode array according to claim 1, wherein signal processing circuitry includes a primary A/D converter and a spare A/D converter.

3. A brain implantable device for control of epilepsy, comprising:
 a multielectrode array with fault-tolerance including a sensor grid composed of a plurality of sensors, the plurality of sensors including primary sensors and spare sensors, wherein each of the primary sensors is linked to an amplifier to define a primary sensor module and each of the spare sensors is linked to an amplifier to define a spare sensor module, the spare sensors being placed in interstitial sites between primary sensors, the multielectrode array also including signal processing circuitry associated with the plurality of sensors identifying faulty primary sensor modules and available spare sensor modules and a control system associated with the sensor grid for replacing faulty primary sensor modules with spare sensor modules via reconfiguration of the plurality of sensors; and
 external circuitry associated with the multielectrode array for receiving EEG signals generated by the multielectrode array;
 wherein each of the primary sensors is linked to an amplifier to define a primary sensor module and each of the spare sensors is linked to an amplifier to define a spare sensor module and the control system replaces faulty primary sensor modules with spare sensor modules.

4. The brain implantable device according to claim 3, wherein signal processing circuitry includes a primary A/D converter and a spare A/D converter.

\* \* \* \* \*